US010188193B2

United States Patent
Rabe et al.

(10) Patent No.: US 10,188,193 B2
(45) Date of Patent: Jan. 29, 2019

(54) APPLICATOR HEADS FOR HANDHELD TREATMENT APPARATUS FOR MODIFYING KERATINOUS SURFACES

(71) Applicant: The Procter & Gamble Company, Cincinnati, OH (US)

(72) Inventors: Thomas Elliot Rabe, Baltimore, MD (US); Faiz Feisal Sherman, Mason, OH (US); Stephan Gary Bush, Liberty Township, OH (US); Stephan James Andreas Meschkat, Bad Soden (DE)

(73) Assignee: The Procter & Gamble Company, Cincinnati, OH (US)

( * ) Notice: Subject to any disclaimer, the term of this patent is extended or adjusted under 35 U.S.C. 154(b) by 545 days.

(21) Appl. No.: 14/807,297

(22) Filed: Jul. 23, 2015

(65) Prior Publication Data

US 2016/0022010 A1 Jan. 28, 2016

Related U.S. Application Data

(60) Provisional application No. 62/028,948, filed on Jul. 25, 2014.

(51) Int. Cl.
*A45D 40/26* (2006.01)
*A61B 5/00* (2006.01)
(Continued)

(52) U.S. Cl.
CPC ........... *A45D 40/261* (2013.01); *A45D 19/02* (2013.01); *A45D 34/04* (2013.01); *A45D 44/005* (2013.01);
(Continued)

(58) Field of Classification Search
CPC ............ A45D 2044/007; A45D 40/261; A45D 19/02; A45D 34/04; A45D 44/005;
(Continued)

(56) References Cited

U.S. PATENT DOCUMENTS 3,323,641 A 6/1967 Landen
5,131,384 A * 7/1992 Obagi .................... A61H 15/02
401/28
(Continued)

FOREIGN PATENT DOCUMENTS

AU 2013200395 A1 3/2015
EP 2314245 A1 4/2011
(Continued)

OTHER PUBLICATIONS

Bioresources Com Et Al: "Peer-Reviewed Article Novel Use of Waste Keratin and Cotton Linter Fibers for Prototype Tissue Papers and Their Evaluation", BioResources, Jul. 26, 2010 (Jul. 26, 2010), pp. 1425-1435.
(Continued)

*Primary Examiner* — Juanita D Jackson
(74) *Attorney, Agent, or Firm* — Melissa G. Krasovec

(57) ABSTRACT

An applicator head is releasably connectable to an outer housing of an apparatus for treating human skin includes a body having a housing connector end having a releasable connecting feature configured to connect to the outer housing and a skin engaging end having an opening therethrough for delivering a skin treatment composition through an opening in the applicator head onto human skin. A pair of skin engagement members is arranged and configured to flatten a surface of the skin.

5 Claims, 14 Drawing Sheets

(51) Int. Cl.
*G06T 7/00* (2017.01)
*H04N 7/18* (2006.01)
*A45D 19/02* (2006.01)
*A45D 34/04* (2006.01)
*A61M 35/00* (2006.01)
*A45D 44/00* (2006.01)
*A45D 34/00* (2006.01)

(52) U.S. Cl.
CPC ............ *A61B 5/0077* (2013.01); *A61B 5/444* (2013.01); *A61B 5/4839* (2013.01); *A61B 5/4848* (2013.01); *G06T 7/0012* (2013.01); *H04N 7/18* (2013.01); *A45D 2034/005* (2013.01); *A45D 2044/007* (2013.01); *A45D 2200/057* (2013.01); *A61B 2560/0431* (2013.01); *A61B 2560/0443* (2013.01); *A61M 35/003* (2013.01); *G06T 2207/30088* (2013.01)

(58) Field of Classification Search
CPC ......... A61B 5/007; A61B 5/442; A61B 5/444; A61B 5/4848; A61B 5/4839
See application file for complete search history.

(56) References Cited

U.S. PATENT DOCUMENTS

| | | | |
|---|---|---|---|
| 5,160,315 A | 11/1992 | Heinecke | |
| 5,308,180 A | 5/1994 | Pournoor | |
| 5,614,310 A | 3/1997 | Delgado | |
| 6,139,829 A | 10/2000 | Estrin | |
| 6,312,124 B1 * | 11/2001 | Desormeaux | B41J 2/16505 347/109 |
| 6,386,692 B1 | 5/2002 | Cowger | |
| 6,461,467 B2 | 10/2002 | Blatchford | |
| 7,166,279 B2 | 1/2007 | Law | |
| 7,841,686 B2 | 11/2010 | Kyoshima | |
| 7,890,152 B2 | 2/2011 | Edgar | |
| 8,007,062 B2 | 8/2011 | Edgar | |
| 8,027,505 B2 | 9/2011 | Edgar | |
| 8,184,901 B2 | 5/2012 | Edgar | |
| 8,231,292 B2 * | 7/2012 | Rabe | A45D 34/041 401/19 |
| 8,297,738 B1 | 10/2012 | Nozawa | |
| 8,695,610 B2 | 4/2014 | Samain | |
| 2003/0060810 A1 | 3/2003 | Syrowicz | |
| 2004/0078278 A1 | 4/2004 | Dauga | |
| 2004/0175347 A1 | 9/2004 | Bissett | |
| 2004/0186373 A1 | 9/2004 | Dunfield | |
| 2004/0230258 A1 | 11/2004 | Yaroslavsky | |
| 2006/0210513 A1 | 9/2006 | Luizzi | |
| 2006/0275237 A1 | 12/2006 | Bissett | |
| 2007/0035815 A1 | 2/2007 | Edgar | |
| 2007/0049832 A1 | 3/2007 | Edgar | |
| 2007/0148120 A1 | 6/2007 | Omura | |
| 2007/0224158 A1 | 9/2007 | Cassin | |
| 2008/0058783 A1 | 3/2008 | Altshuler | |
| 2008/0194971 A1 | 8/2008 | Edgar | |
| 2008/0317539 A1 | 12/2008 | Brugger | |
| 2009/0025747 A1 | 1/2009 | Edgar | |
| 2009/0131922 A1 | 5/2009 | Dewey | |
| 2010/0224205 A1 | 9/2010 | Mitra | |
| 2010/0224211 A1 | 9/2010 | Rabe | |
| 2011/0129283 A1 | 6/2011 | Samain | |
| 2011/0155161 A1 | 6/2011 | Samain | |
| 2011/0159463 A1 | 6/2011 | Samain | |
| 2011/0162673 A1 | 7/2011 | Samain | |
| 2012/0113171 A1 | 5/2012 | Murata | |
| 2014/0163487 A1 | 6/2014 | Tout | |
| 2015/0359315 A1 | 12/2015 | Rabe | |
| 2015/0359712 A1 | 12/2015 | Rabe | |
| 2015/0359714 A1 | 12/2015 | Rabe | |
| 2015/0360015 A1 | 12/2015 | Rabe | |
| 2015/0360016 A1 | 12/2015 | Rabe | |
| 2015/0360017 A1 | 12/2015 | Rabe | |
| 2016/0022006 A1 | 1/2016 | Rabe | |
| 2016/0022008 A1 | 1/2016 | Rabe | |
| 2016/0022009 A1 | 1/2016 | Rabe | |
| 2016/0022010 A1 | 1/2016 | Rabe | |
| 2016/0022011 A1 | 1/2016 | Rabe | |
| 2016/0022972 A1 | 1/2016 | Rabe | |

FOREIGN PATENT DOCUMENTS

| | | |
|---|---|---|
| FR | 2933585 B1 | 10/2011 |
| JP | 3101962 A | 4/1991 |
| JP | 9141846 A | 6/1997 |
| JP | 2001314226 | 11/2001 |
| JP | 2003054007 | 2/2003 |
| JP | 2006297691 A | 11/2006 |
| JP | 2007320066 A | 12/2007 |
| JP | 2010513091 A | 4/2010 |
| JP | 2011189342 A | 9/2011 |
| WO | WO2008/098234 A2 | 8/2008 |
| WO | WO2008/098235 A2 | 8/2008 |
| WO | WO2008/100878 A1 | 8/2008 |
| WO | WO2009/036876 | 3/2009 |
| WO | WO2010/004531 | 1/2010 |
| WO | WO2013/144186 A1 | 10/2013 |
| WO | WO2014028572 A2 | 2/2014 |

OTHER PUBLICATIONS

ISR PCT/US2015/041887; dated Dec. 15, 2015; 18 pages.
ISR PCT/US2015/041887; dated Oct. 22, 2015; 7 pages.
ISR PCT/US2015/041888; dated Nov. 5, 2015; 14 pages.
ISR PCT/US2015/041889; dated Oct. 14, 2015; 12 pages.
ISR PCT/US2015/0418880; dated Oct. 7, 2015; 12 pages.
ISR PCT/US2015/0418881; dated Oct. 28, 2015; 12 pages.
ISR PCT/US2015/0418882; dated Oct. 28, 2015; 11 pages.
U.S. Appl. No. 14/807,140, filed Jul. 23, 2015, Thomas Rabe.
U.S. Appl. No. 14/807,231, filed Jul. 23, 2015, Thomas Rabe.
U.S. Appl. No. 14/807,257, filed Jul. 23, 2015, Thomas Rabe.
U.S. Appl. No. 14,807,360, filed Jul. 23, 2015, Thomas Rabe.
Search Report and Written Opinion for PCT/US2015/041881 dated Oct. 28, 2015.
All Office Actions for U.S. Appl. No. 14/807,140, filed Jul. 23, 2015.
All Office Actions for U.S. Appl. No. 14/807,198, filed Jul. 23, 2015.
All Office Actions for U.S. Appl. No. 14/807,257, filed Jul. 23, 2015.
All Office Actions for U.S. Appl. No. 14/807,360, filed Jul. 23, 2015.
All Office Actions for U.S. Appl. No. 14/736,524, filed Sep. 14, 2015.
All Office Actions for U.S. Appl. No. 14/736,534, filed Jun. 11, 2015.
All Office Actions for U.S. Appl. No. 14/736,551, filed Jun. 11, 2015.
All Office Actions for U.S. Appl. No. 14/736,563, filed Jun. 11, 2015.
All Office Actions for U.S. Appl. No. 14/736,584, filed Jun. 11, 2015.
All Office Actions for U.S. Appl. No. 14/736,507, filed Jun. 11, 2015.
All Office Actions for U.S. Appl. No. 15/349,073, filed Nov. 11, 2016.

* cited by examiner

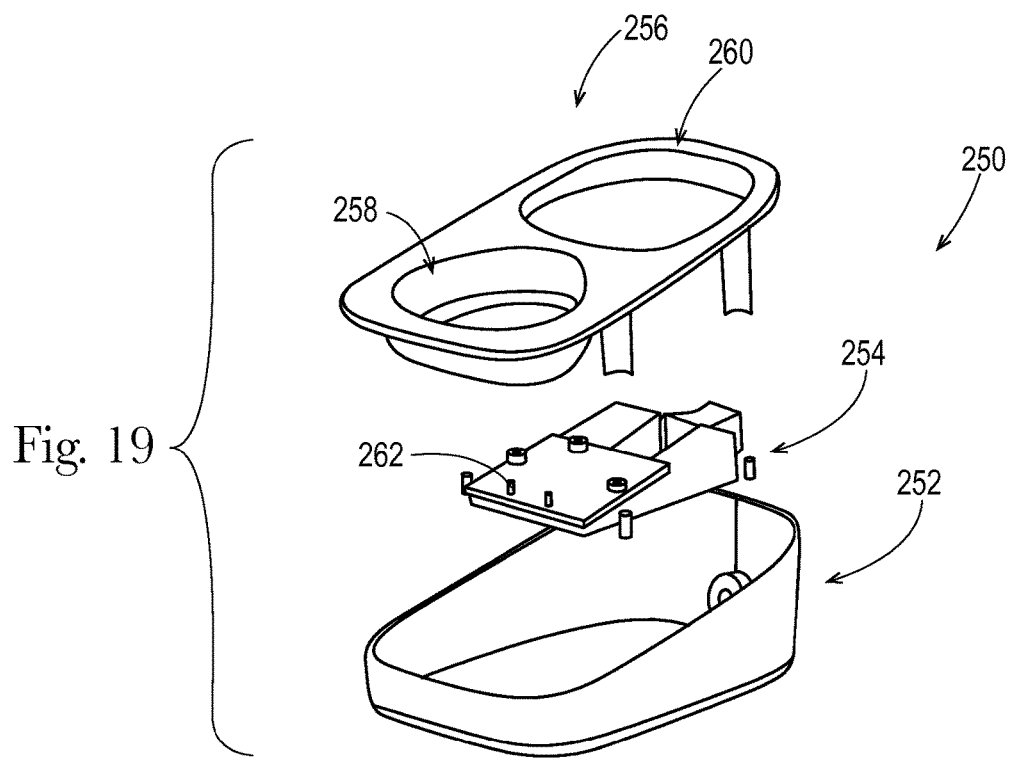
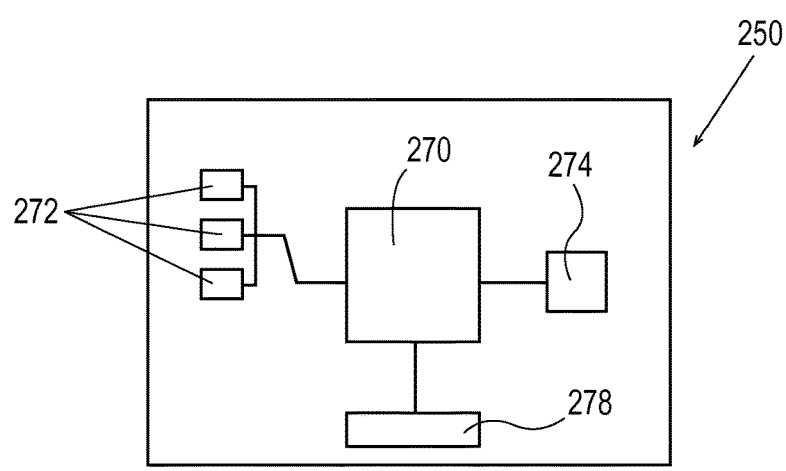

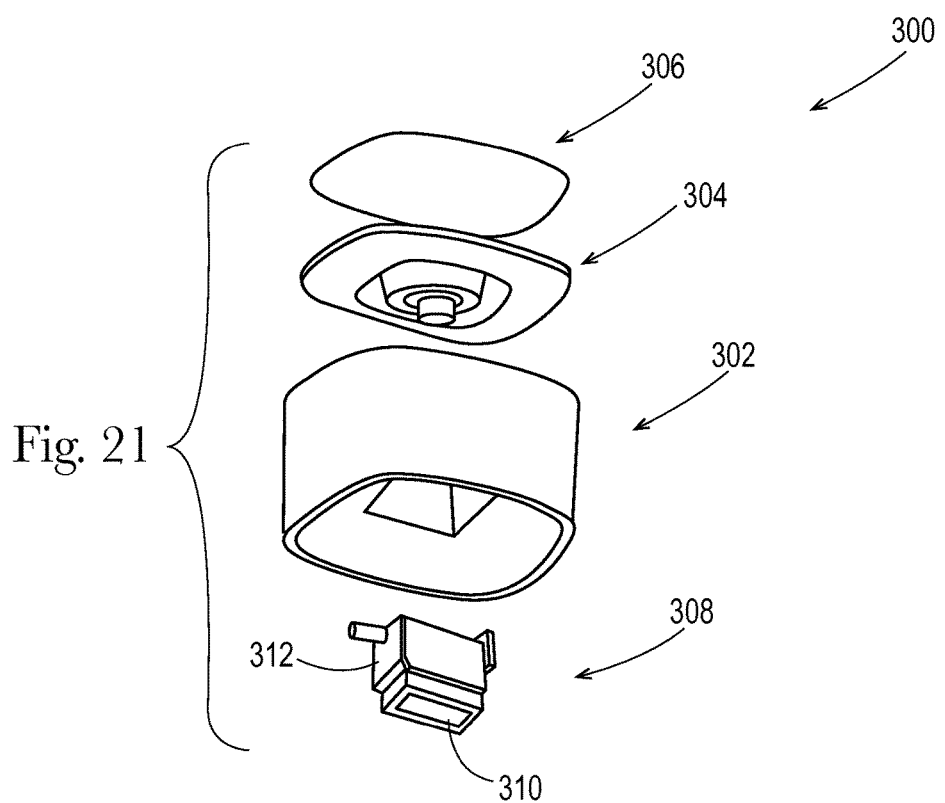

APPLICATOR HEADS FOR HANDHELD TREATMENT APPARATUS FOR MODIFYING KERATINOUS SURFACES

FIELD

The present application relates to a handheld treatment apparatus for applying compositions to skin, and other keratinous surfaces. The compositions can modify color or structure of the keratinous surface.

BACKGROUND

Tonal variations on human skin have multiple causes. Acne, freckles, sun damage, and age spots are just a few of the common causes of visible defects on skin. Textural variations such as fine lines, wrinkles and scars are also well known. Both tonal and textural deviations are noticeable to the human eye, even when they are quite small. Covering large areas of skin on and around deviations with makeup or other concealers is known.

Moreover, attempts have been made at more precise, and localized application of compositions that hide, or cover-up skin deviations. Handheld devices that are moved across the skin have been developed to apply skin treatment compositions to local defects. But these devices have been plagued by the absence of two necessary components, speed and accuracy. For these handheld devices to work effectively, they must find the defects quickly, and treat them immediately. Finding a spot on the skin is of little use if the user has moved the applicator head to a different area of the skin before the spot can be effectively treated.

Therefore, there exists a need for methods and apparatuses that can quickly and precisely detect tonal and textural defects on skin. Then with equal speed and precision, apply treatment compositions directly to the deviations. These methods and apparatuses are defined by the present specification.

SUMMARY

In an embodiment, an applicator head is releasably connectable to an outer housing of an apparatus for treating human skin includes a body having a housing connector end having a releasable connecting feature configured to connect to the outer housing and a skin engaging end having an opening therethrough for delivering a skin treatment composition through an opening in the applicator head onto human skin. A pair of skin engagement members is arranged and configured to flatten a surface of the skin.

In another embodiment, an apparatus for treating human skin includes an outer housing including a graspable portion and an applicator portion comprising an applicator head and at least one nozzle in the applicator portion having a main axis for delivering a skin treatment composition through an opening in the applicator head onto human skin. An image capture device captures images of the human skin through the opening. A processor analyzes the images of the human skin to identify skin deviations. A pair of skin engagement members arranged and configured to flatten a surface of the skin.

In another embodiment, a method of treating human skin using a handheld treatment apparatus is provided. The method includes delivering a skin treatment composition through an opening in a first applicator head releasably connected to an outer housing and onto human skin. Images of the human skin are captured using an image capture device of the handheld treatment apparatus though the opening. The images of the human skin are analyzed to identify skin deviations using a processor. The first applicator head is removed. A second applicator head is releasably connected to the outer housing. The second applicator head being different from the first applicator head.

Embodiments described herein can solve many problems with prior devices and methods. Specifically, tonal variations on skin can be more accurately and quickly detected. The speed with which a skin deviation can be found and identified is critical because the applicator is continuously moving across the skin. The quicker the deviation can be identified, the quicker the applicator nozzle, or nozzles can be activated. The quicker the nozzles are activated the more likely the skin treatment composition will hit the deviation precisely. This allows for the optimal coverage of the deviation, and minimal coverage on the areas of natural skin that do not need treatment. Thus, the simpler the detection algorithm is, and the simpler the apparatus is that implements the algorithm is, the quicker and more precise the overall correction process is. This is a substantial improvement over more complicated, slower and less precise apparatuses and methods of the past.

BRIEF DESCRIPTION OF THE DRAWINGS

While the specification concludes with claims particularly pointing out and distinctly claiming the present invention, it is believed the same will be better understood from the following description taken in conjunction with the accompanying drawing in which:

FIG. 19 illustrates a base station for use with the handheld treatment device of FIG. 1 according to one of more embodiments described herein;

FIG. 20 is a schematic representation of the base station of FIG. 19 according to one or more embodiments described herein; and FIG. 21 illustrates a cap assembly for use with the handheld treatment apparatus of FIG. 1 according to one or more embodiments described herein.

DETAILED DESCRIPTION

Embodiments described herein may be understood more readily by reference to the following detailed description. It is to be understood that the scope of the claims is not limited to the specific compositions, methods, conditions, devices, or parameters described herein, and that the terminology used herein is not intended to be limiting. Also, as used in the specification, including the appended claims, the singular forms "a," "an," and "the" include the plural, and reference to a particular numerical value includes at least that particular value, unless the context clearly dictates otherwise. When a range of values is expressed, another embodiment includes from the one particular value and/or to the other particular value. Similarly, when values are expressed as approximations, by use of the antecedent basis "about," it will be understood that the particular values form another embodiment. All ranges are inclusive and combinable.

The term "frexel" is defined as a small pixel-like region of the keratinous surface. A frexel might correspond to a small portion of a freckle or other skin feature, or it may correspond to an area of the keratinous surface that does not have special features. The term frexel is used to suggest that what is being measured is on a 3-D surface rather than a flat surface. A region of keratinous surface is comprised of a plurality of frexels. For instance, if a resolution of 300 dots per inch (11.8 dots per mm or "dpmm") is used, a frexel may have a width and height of about $\frac{1}{300}$th of an inch (0.085 mm) so that there are approximately 90,000 frexels per square inch (about 140 frexels per square mm). The surface of the human body may have millions of frexels.

All percentages and ratios used herein are by weight of the total composition, and all measurements made are at 25° C., unless otherwise designated.

Figure 1:
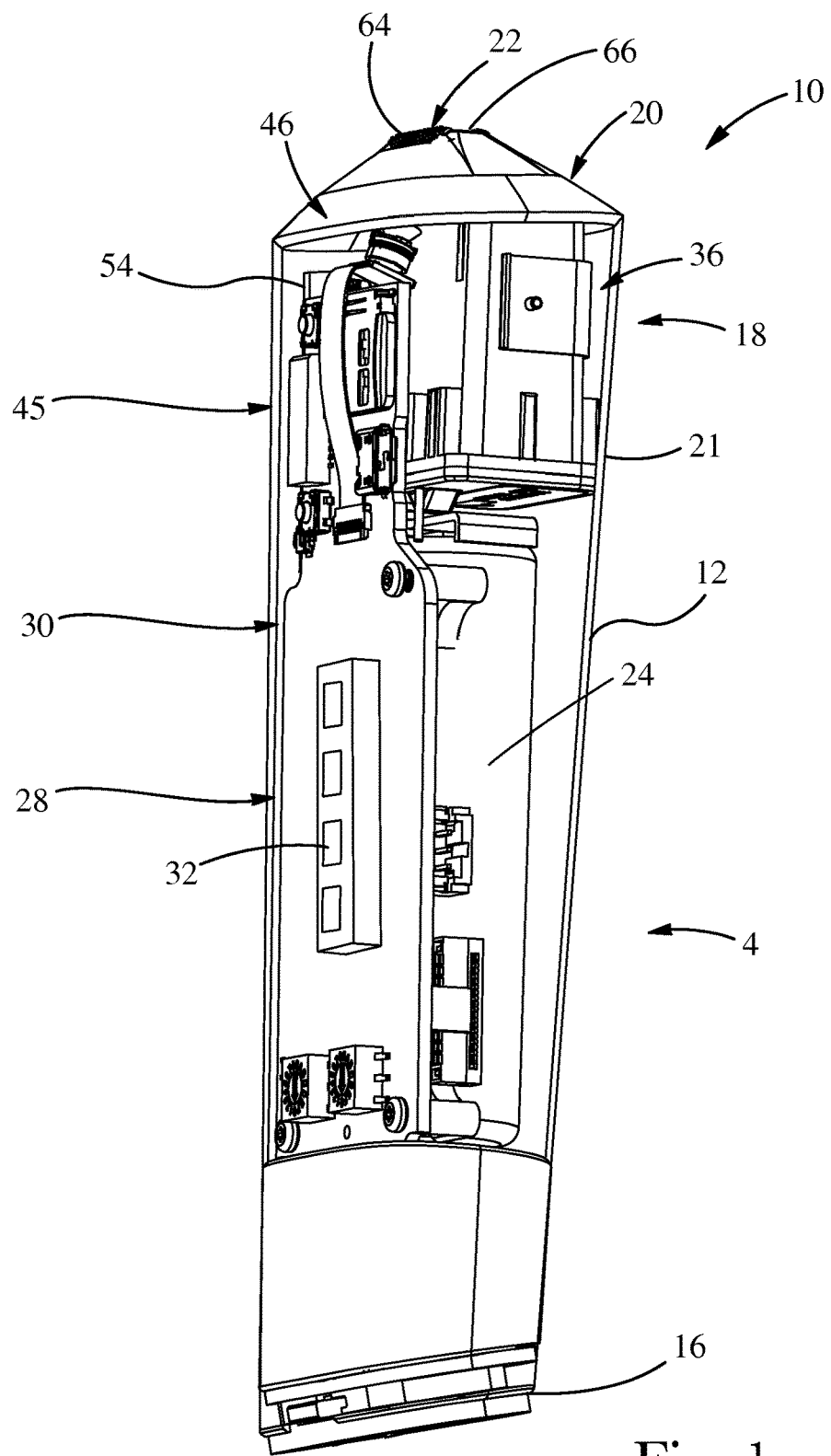
FIG. 1 illustrates a side view of a handheld treatment apparatus according to one or more embodiments described herein.

Referring to FIG. 1, a handheld treatment apparatus 10 for applying treatment compositions to skin or other surfaces generally includes an outer housing 12, which is shown transparent for illustrative purposes that is sized and shaped to be held in-hand and manipulated manually during a treatment operation. The outer housing 12 includes a graspable portion 14 including a base 16 and an applicator portion 18 including an applicator head 20 having an opening 22 through which a skin treatment composition can be delivered to the skin. A battery 24 (e.g., a rechargeable battery a primary battery, an electrochemical capacitor, a double-layer capacitor, a supercapacitor or a hybrid battery-capacitor) and an on/off mechanical or voice activated switch may be located in the graspable portion 14 of the outer housing 12. In other embodiments, the handheld treatment apparatus 10 may not include a battery or the handheld treatment apparatus 10 may be plugged, for example, to an electrical supply outlet. In some embodiments, the graspable portion 14 including the base 16 may include lighting for illuminating the base 16 or other locations of the outer housing 12. Also, the lighting may be used to illuminate the skin surface to facilitate operator use. A user interface 28 may also be provided where a user can provide inputs or control instructions to a processing unit 30 for controlling the handheld treatment apparatus 10. While various buttons or touch areas 32 (e.g., utilizing capacitive touch sensors, momentary switches, etc.) are illustrated for the user to touch and activate, any other suitable input devices may be used, such as touch screen displays, voice commands, etc. In some embodiments, the handheld treatment apparatus 10 may be capable of wired or wireless communication and be controlled remotely, e.g., using a cell phone or other handheld or portabale computing device, or capable of otherwise sending information wirelessly or wired to an external device, for example, for tracking treatment results.

The applicator portion 18 may include the applicator head 20 including the opening 22 through which the skin treatment composition can be delivered to the skin and a cartridge 36 that is located within the outer housing 12. In some embodiments, the applicator portion 18 may have a removable or otherwise moving portion 21 (e.g., sliding, pivoting, snapping, etc.) that can be moved to provide access to the cartridge 36. As will be described in greater detail below, the cartridge 36 may include a nozzle array that is embedded in a cartridge die. In other embodiments, separate nozzles may be used that can be connected to the cartridge. The applicator head 20 can provide a space between the skin surface at the opening 22 and the nozzle array (and other components) during use. An image capture device 46 may also be located at the applicator portion 18 and adjacent the cartridge 36. The image capture device 46 can be any of a variety of commercially available devices such as a digital camera that takes black and white or color images, a spectrophotometer or similar devices that are sensitive to electromagnetic energy wavelengths. The image capture device 46 takes a picture of the skin and sends it to the processing unit 30. The processing unit 30 may be generally referred to as a central processing unit, or CPU, which may comprise a simple circuit board, a more complex computer, or the like. The CPU unit or device may include Application Specific Integrated Circuit (ASIC), controller, Field Programmable Gate Array (FPGA), integrated circuit, microcontroller, microprocessor, processor, and the like. The CPU may also include memory functionality, either internal to the CPU as cache memory, embedded memory, Random Access Memory (RAM), Static Random Access Memory (SRAM) and the like or external to the CPU for example as Dynamic Random-Access Memory (DRAM), Read Only Memory (ROM), Static RAM, Flash Memory (e.g., Compact Flash or SmartMedia cards), disk drives, Solid State Disk Drives (SSD), embedded memory, or even Internet Cloud storage. The image may be analyzed by the processing unit 30 to identify skin deviations as will be described below. A pen driver 45 may be provided to facilitate communication with the processing unit 30 with external devices (e.g., for tracking treatments, such as skin tone affects, time of use, etc.) A variety of lighting may also be provided to illuminate the skin area such that the image capture device can have constant illumination. The lighting can be, for example, a light emitting diode (LED), incandescent light, fluorescent light, neon bulb, or any other suitable light source.

Figure 2:
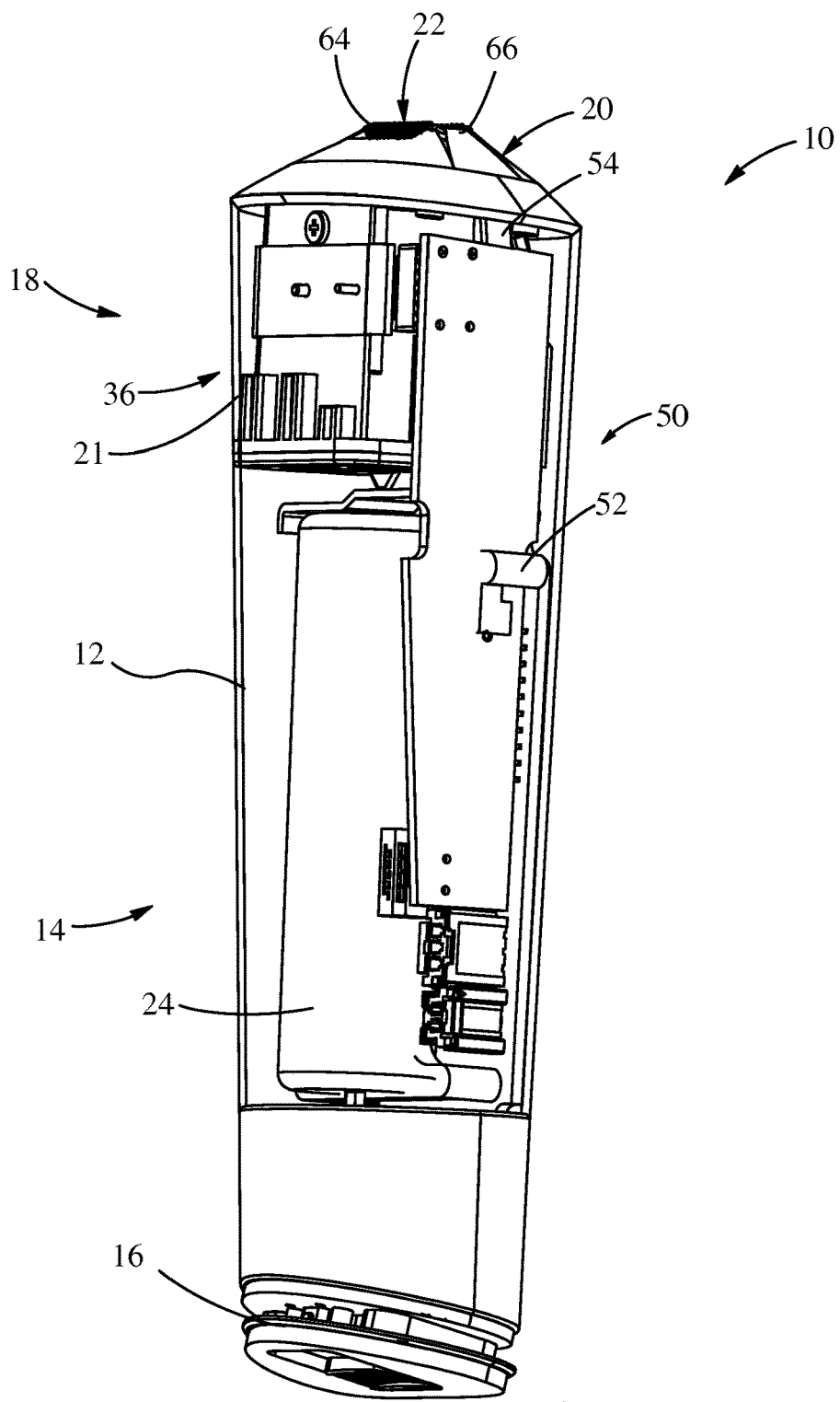
FIG. 2 illustrates another side view of the handheld treatment apparatus of FIG. 1.

Referring to FIG. 2, lighting may be employed for uses other than or in addition to image capture for treatment composition delivery. For example, a bulge detection system 50 may be included utilizing lighting to emphasize three-dimensional skin surface features, such as a bulge of skin at the opening 22, which can affect delivery of the treatment composition to the skin surface. The bulge of skin may be due to, for example, excessive pressure applied to the skin surface during use. Three-dimensional skin surface features can be emphasized using lighting incident on the skin surface at an angle to the skin surface to create a shadowing effect (as opposed to perpendicular to the skin surface). As an example, a light source 52, such as an LED may be provided that can generate light that strikes an angled mirror

Figure 3:
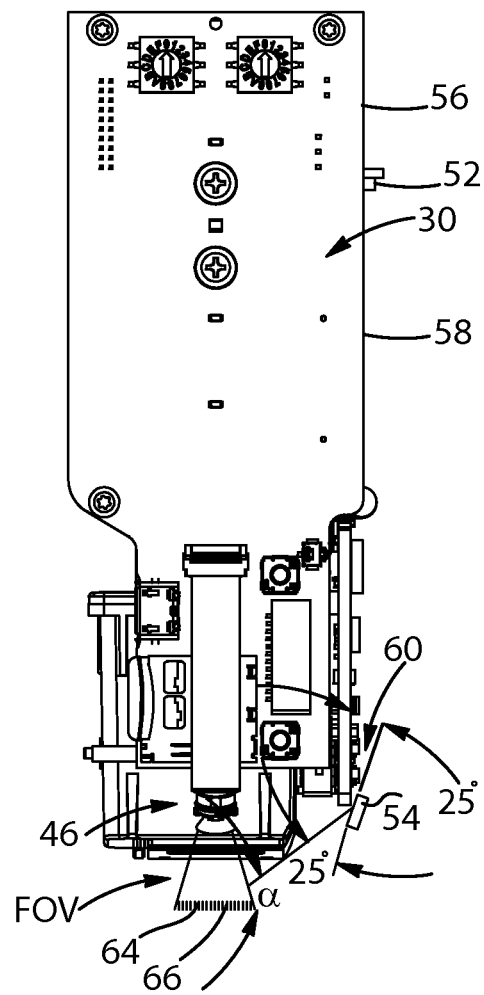
FIG. 3 illustrates a detail view of a bulge detection system for the handheld treatment apparatus of FIG. 1 according to one or more embodiments described herein.

54. Referring also to FIG. 3, the light source 52 may be provided, for example, as part of a circuit board 56 that generates a light beam 58 traveling alongside the circuit board 56 toward the mirror 54. An opening or slit 60 may be provided between the mirror 54 and its support structure, in this instance, the circuit board 56 to allow the light beam 58 to pass therethrough and reflect off of the mirror 54 with the mirror 54 in the desired angled position. Mirror 54 may also be a prism, a diffraction grating or similar structure that bends light beam 58 so that it illuminates the bulge of skin at the opening 22. Alternatively, a light guide (for example a fiber optic thread, optical wave guide, etc,) may be used to transport the light beam 58 from the light source 52 to the mirror 54 or to the bulge of skin at the opening 22

In order to provide lighting incident on the skin surface at an angle to the skin surface, the mirror 54 can be located outside the field of view (FOV) of the image capture device 46 and angled to direct the light from the light source 52 toward the skin surface and at a location within the FOV at an angle α to the skin surface, such as no greater than about 45 degrees, such as no greater than about 25 degrees, such as between about 20 degrees and about 30 degrees. Where a bulge is present in the skin, a light contrast gradient may be formed on the skin surface that the captured by the image capture device 46 and analyzed by the processing unit 30 (or a different processing unit). As can be appreciated, the light gradient formed for a bulged skin surface may be different from the light gradient formed for a relatively smooth or non-bulged skin surface. For example, a skin surface with a relatively large bulge may have a contrast gradient that transitions from light to dark relatively abruptly while a skin surface that has no bulge may have a relatively smooth contrast gradient from light to dark. The processing unit 30 may include logic that is used to identify out-of-parameter contrast gradient features that may indicate excessive bulging of skin above a predetermined threshold. If such a parameter or excessive bulging condition is detected, an indication may be provided to the user by the handheld treatment apparatus 10, such as vibration, sound, light, tactile, etc. In some embodiments, a pause condition may be initiated by the processing unit 30 halting a treatment operation until the bulge is no longer detected. The handheld treatment apparatus 10 may also utilize a pressure sensor that is configured to provide an indication of pressure to the processing unit 30, which may also be indicative of presence of bulging producing similar indications to the user.

Figure 4:
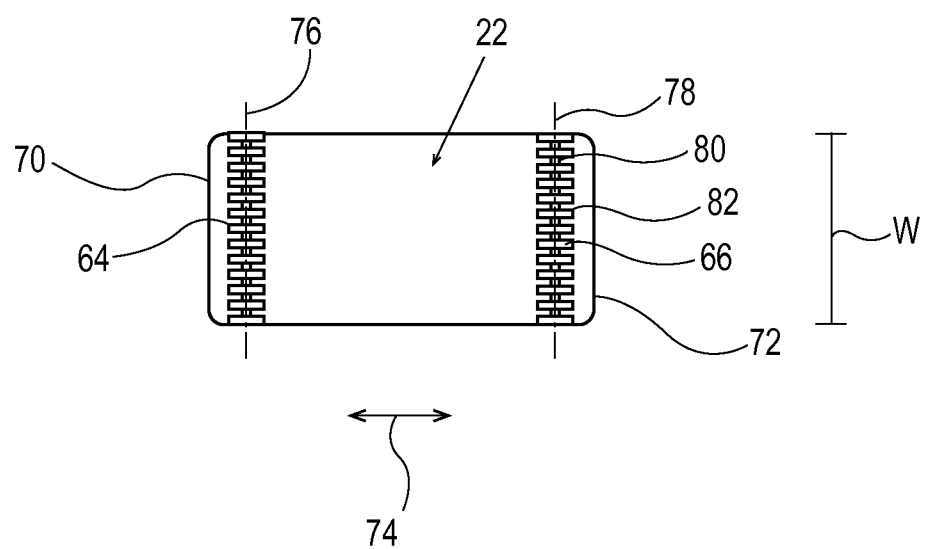
FIG. 4 illustrates a skin engagement member arrangement for the handheld treatment apparatus of FIG. 1 according to one or more embodiments described herein.

Referring to FIGS. 1-3, one or more skin engagement members, in this example, rollers 64 and 66 may be provided at the opening 22. The rollers 64 and 66 may be provided for a number of reasons including to maintain contact between the handheld treatment apparatus 10 and the skin surface, to reduce friction between the skin and the handheld treatment apparatus 10 while moving the handheld treatment apparatus 10 across the skin and to present a relatively flat skin surface to the image capture device 46 and nozzle array. FIG. 4 illustrates the rollers 64 and 66 in isolation with the opening 22 formed in the applicator head 20. In this embodiment, the rollers 64 and 66 are located at opposite edges 70 and 72 of the opening 22, extending continuously across a width W of the opening 22. Opening 22 may be shaped as a square, rectangle, parallelogram, polygon, circle, etc. In this way, the rollers 64 and 66 define forward and rearward rolling directions (represented by arrows 74) perpendicular to their axes of rotation 76 and 78 for the handheld treatment apparatus 10 where the rollers 64 and 66 can be rolled over the skin surface with the rolling motion essentially in the same direction of motion as the handheld treatment apparatus 10. In some embodiments, the opening 22 has an area that is less than 1000 mm$^2$ and preferably less than 100 mm$^2$. The rollers are connected to the applicator head at a pivot axis, with a distance between the pivot axes between about 5 mm and about 15 mm.

As illustrated, the rollers 64 and 66 may be continuous along their entire lengths and each roll as a single unit. In other embodiments, multiple rollers may be used along the edges 70 and 72, capable of independent rotation. The rollers 64 and 66 may have a surface feature that can be used to reduce contact between the surface of the rollers 64 and 66 and the skin surface (e.g., to reduce smearing or displacement of the skin treatment composition). For example, the rollers 64 and 66 may be provided with grooves 80 of reduced diameter to provide peaks 82 that roll against the skin surface. Any other suitable surface features may be used, such as frustoconical projections, spikes, etc. that allow for rolling against the skin while presenting a relatively flat skin surface within the opening 22. The rollers 64 and 66 may be formed of any suitable materials, such as plastic rubber, ceramic, metal, stainless steel and may be coated with for example Teflon, polyimide or parylene to reduce rolling, friction. The rollers may also be gliders, sliders, balls or spheres moving along the skin surface and they may be flat, curved, meshed or coated to work like the rollers 64 and 66. The rollers may also have markings on them visible to the image capture device 46 so that they can provide reference points for measuring motion, speed, position, etc. of the handheld treatment apparatus 10.

Figure 5:
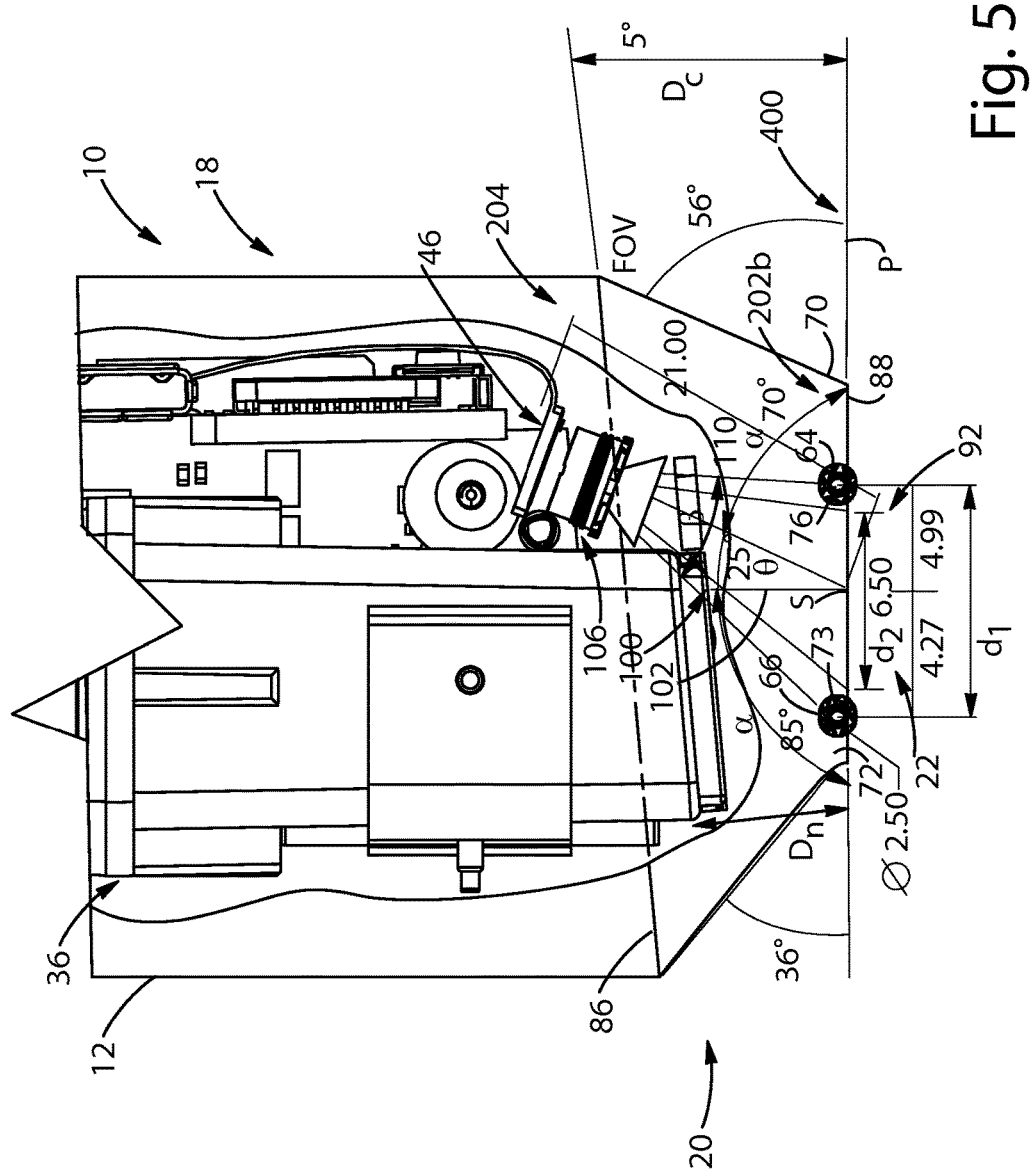
FIG. 5 is a detail view of the handheld treatment apparatus of FIG. 1 showing the applicator head according to one or more embodiments described herein.

Referring to FIG. 5, the applicator portion 18 of the handheld treatment apparatus 10 is illustrated with the outer housing 12 being again shown transparent for illustrative purposes. As can be seen, the applicator head 20 includes a body having a housing connector end 86 and a skin engaging end 88 having the opening 22. In some embodiments, the head may be removeable (and interchangeable with other heads) with the housing connector end 86 having a releasable connection (e.g., tongue and groove, threaded, snap, etc.) with the outer housing 12. In some embodiments, the applicator head 20 may have a wired or wireless connection with the processing unit 30 for communication therebetween. The head 20 is somewhat cone or frustoconical in shape, decreasing in width from the housing connector end 86 to the skin engaging end 88. While the applicator head 20 is shown being somewhat cone-shaped or rounded, it can be of any suitable shape, such as box-shaped, spherical, polygonal, etc.

The rollers 64 and 66 are located at the opposite edges 70 and 72 of the opening 22. The rollers 64 and 66 have outer diameters (e.g., about 2.5 mm) that are sized to extend beyond the edges 70 and 72 for contacting the skin surface, which, for purposes of description, can be represented by a plane P that is tangent to both of the rollers 64 and 66 outside of the head 20, herein referred to as "an imaginary flat rolling surface." The rollers 64 and 66 each rotate around their axes 76 and 78 that are spaced apart a distance $d_1$ (e.g., between about 6 mm and about 15 mm) with a distance $d_2$ (e.g., between about 1 mm and about 10 mm) between the rollers 64 and 66, thereby providing a gap 92 for imaging the skin surface at a location between the rollers 64 and 66. It should be noted that the handheld treatment apparatus 10 may be provided with multiple heads having rollers of various spacing, diameters and surface features. As one example, an applicator head having reduced spacing between rollers may be chosen such that skin bulge detection may not be needed. In another embodiment, the rollers may rotate at difference speeds (i.e., rpm) or have different levels of rolling resistance to create tension on the skin surface, effectively stretching the skin as the handheld treatment apparatus 10 rolls across the skin surface.

As noted above, the applicator head 20 also provides spacing for the cartridge 36, its associated nozzle array 100 and the image capture device 46 from the imaginary flat rolling surface P. As will be described in greater detail below, such an arrangement can provide a desired controlled randomness to treatment composition delivery precision, while spacing imaging components away from the skin surface during treatment delivery. In the illustrated embodiment, the nozzle array 100 may be spaced from the imaginary flat rolling surface P by a fixed distance $D_n$ of at least about 4 mm, such as at least about 6 mm, such as at least about 8 mm, such as at least about 10 mm, such as between about 4 mm and about 12 mm and defines one axis of the volume through which the nozzles deliver the treatment composition. The nozzle array 100 of the cartridge 36 may also be offset from perpendicular to the imaginary flat rolling surface P such that a main axis 102 of the nozzle array 100 (the nozzles of the nozzle array may have parallel main axes aligned in a row) may be at an angle $\alpha$ less than 90 degrees (e.g., about 85 degrees or less) to the imaginary flat rolling surface P. As used herein, the "main axis" of a nozzle is a straight line passing through the geometrical center of the nozzle and intersecting the imaginary flat rolling surface P.

The image capture device 46 may be recessed further away from the imaginary flat rolling surface P than the nozzle array 100. Such an arrangement can reduce the possibility of contamination of the image capture device 46 by the treatment composition carried by the cartridge 36. For example, the image capture device 46 may include a lens portion 106 that is spaced from the imaginary flat rolling surface P a distance $D_c$ of greater than about 4 mm, such as greater than about 6 mm, such as greater than about 8 mm, such as greater than about 10 mm, such as greater than about 12 mm. The image capture device has an FOV of an angular dimension $\beta$. As used herein, "field of view" is the region that is visible by the image capture device. The FOV of the image capture device 46 extends between the rollers 64 and 66, through the opening 22 to image the skin surface. In some embodiments, the FOV of the image capture device 46 may include the rollers 64 and 66. Imaging of the rollers 64 and 66 can allow, for example, speed and position detection using the processing unit 30 through image analysis. For example, the rollers 64 and/or 66 may include markers, such as colors, that can be used by the processing unit 30 to determine speed of the handheld treatment apparatus 10 rolling along the skin surface. In some embodiments, the FOV of the image capture device 46 may include parts of the rollers 64 and 66 and parts of their markings. In some embodiments, the FOV may be adjustable (e.g., using user interface 28) or fixed (i.e., non-adjustable). In some embodiments, the FOV may be about 50 mm² or more, such as 70 mm² or more, such as 80 mm² or more.

The image capture device 46 may include an optical axis 110 that is offset from perpendicular to the imaginary flat rolling surface P. As used herein, the "optical axis" of the image capture device is a straight line passing through the geometrical center of the lens of the image capture device and intersecting the imaginary flat rolling surface P. In some embodiments, the optical axis 110 may be at an angle $\gamma$ of less than 90 degrees, such as less than about 85 degrees, such as less than about 75 degrees, such as less than about 65 degrees from the imaginary flat rolling surface P. In the illustrated embodiment, the main axis 102 of the nozzle array 100 intersects the FOV and meets the optical axis 110 of the image capture device 46 at the same focal point S (representing a line extending along the parallel axes of the array of nozzles) on the imaginary flat rolling surface P. In some embodiments, an included angle $\theta$ between the optical axis 110 and the main axis 102 may be at least about 10 degrees, such as at least about 15 degrees, such as at least about 25 degrees, but less than about 45 degrees. The optical axis passes between rollers 64 and 66.

Figure 6:
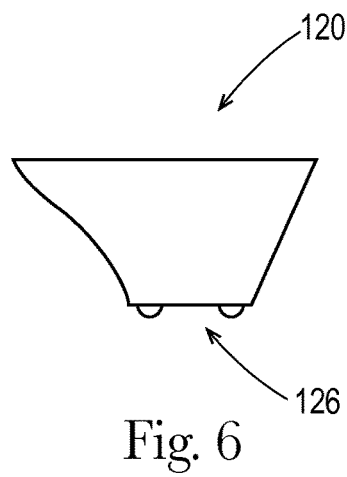
FIGS. 6 and 7 illustrate two different embodiments of interchangeable applicator heads.
Figure 7:
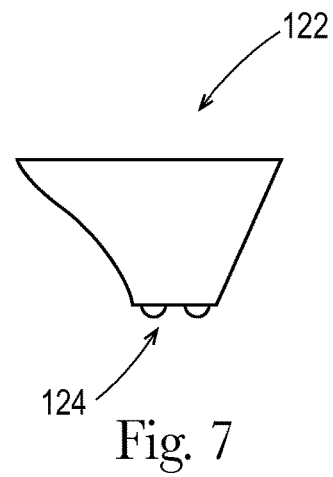
Figure 8:
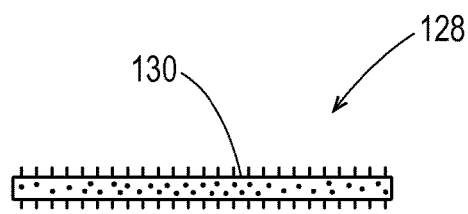
FIGS. 8-10 illustrate different roller embodiments for use with an applicator head.
Figure 9:
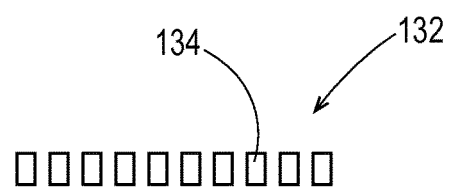
Figure 10:
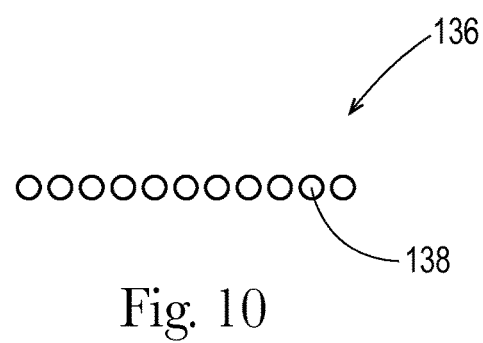

Referring to FIGS. 6 and 7, a pair of applicator heads 120 and 122 is illustrated. As indicated above, the applicator heads 120 and 122 may each be removeable from the outer housing 12 and may also be interchangeable. As an example, the applicator head 122 may have an opening 124 that is smaller than an opening 126 of the applicator head 120. Providing applicator heads with different geometries can allow for configurations that are more tailored to a particular skin application area. Further, while continuous, elongated rollers 64 and 66 are illustrated above, FIGS. 8-10 illustrate other roller configurations. For example, roller 128 of FIG. 8 may include spikes or other projections 130. Roller 132 of FIG. 9 may be divided into multiple, individual wheels 134 and roller 136 of FIG. 10 may include multiple, individual spheres or ball bearings 138.

Operation of the handheld treatment apparatus 10 is directed to analyzing and treating tonal imperfections on human skin that comprises the steps of taking at least one background image of at least $10\mu^2$ of skin and then calculating the average background L value of the image on a grey scale. Further, a treatment image of the skin is acquired and from that image a localized L value is calculated for individual pixels or a group of pixels. The local L value is then compared to the background L value to identify skin deviations. A skin deviation is an area of skin where the difference between the two L values is greater than a predetermined $\Delta L$ value. The skin deviations are then treated with a treatment composition having a predetermined or variable contrast ratio.

The handheld treatment apparatus 10 has the applicator head 20 that includes the array of nozzles 100 and a reservoir (e.g., cartridge 36) for containing the skin treatment composition. The image capture device 46 can take an image of at least $10\mu^2$ of skin and the processing unit 30 can analyze the image to calculate the average background L value. The image capture device 46 then can take a subsequent image of the skin and calculate the localized L value of individual pixels or groups of pixels of skin. The processing unit 30 can then compare the local L value to the background L value to identify skin deviations where the difference between the two L values is greater than a predetermined value. While it is anticipated that a remote processing unit, either tethered to the device, or which communicates wirelessly, can be used, a local processing unit within the handheld treatment apparatus 10 is exemplified herein. Size and speed of the processing unit 30 and associated memory is an important consideration of the design parameters, but cost and other considerations can be considered.

The predetermined $\Delta L$ is the absolute value of the difference between the local L and the background L. This value, $\Delta L$, can be measured in absolute numbers or as a percentage. The images can be taken, or converted to a standard grey scale. Any numerical scale that measures lightness to darkness can be considered a "grey scale." Further, the background L value should not be too close to the ends of this scale. For example, if the grey scale is 0-100, with 0 being pure black and 100 being pure white, a background in the 0-10 range, or in the 90-100 range may be too light or too dark to show meaningful differences. Accordingly, one can adjust the background lighting, or the gain on the image capture device 46 taking the image, to move the background L closer to the middle of the scale. In this example, a background L of 50 would be ideal, with a background L in the range of 10-90 preferred, 20-80 even more preferred.

The most common grey scale is 0-255 (no units) and other examples include 0-1024 and 0-4096. For a grey scale of 0-255, the difference between grey scale steps is at least 1/255. In this example, it may be desirable to use image capture device and lighting settings that provide a background L value between 60 and 210. Using the 0-255 gray scale the ΔL is preferably at least 0.5, more preferably at least 1 and even more preferably at least 1.5, to initiate treatment of the skin. Likewise, ΔL can be measured as a percentage, for example, a numerical ΔL of 2.6 is approximately equal to 1.0% of a 255 grey scale. Thus ΔL may be plus or minus 0.25%, preferably plus or minus 0.5% even more preferably plus or minus 0.75%, of the grayscale.

The skin treatment compositions may be used to hide, or more appropriately, to camouflage a skin deviation are described and exemplified in greater detail below. One characteristic of the skin treatment compositions is the contrast ratio. The contrast ratio of the treatment composition when treating the skin may be at least 0.1. The skin lightness and treatment composition lightness can be measured by a calibrated spectrophotometer. In the case of using a calibrated spectrophotometer, the average L value of human skin usually spans the range of about 25 to 75. In this case the corresponding treatment composition has a lightness value of at least 2 units greater, preferably at least 3 units greater, and even more preferably at least 5 units greater than the average skin lightness value of the consumer.

Images may be taken in sequence or preferably continuously. For example, a camera that takes a minimum of 4 frames per second may be used, for example greater 100 frames per second and even greater than 200 frames per second, and even greater than 600 frames per second. Higher speed cameras (greater than 4 frames per second) may also be used. All images may be taken in a grey scale or converted to a grey scale, the grey scale can have any range, for example, 0-255, no units. This corresponds approximately to a refresh rate of 0.2 seconds or faster. Consistent with the camera, the CPU processes at a rate of 100 frames per second and even greater than 200 frames per second and even greater than 600 frames per second.

There is no technical difference between an image used for background L values and those used for local L values, the difference is in the analysis of the image. Hence, the images may be continually sent from the image capture device 46 to the processing unit 30 to calculate the L values, and ΔL values. It is understood, that the background L can be calculated once in a treatment period and that value reused throughout the treatment period. Or, it can be continually recalculated as long as the treatment process goes on. Moreover, there can be pre-programmed triggers to initiate a recalculation of the background L. For example, if an extended period of time elapses (for example, about 10 seconds) and no skin deviations are found, or if skin deviations are being found too frequently, a new background L might automatically be calculated.

When the ΔL exceeds the predetermined value, the skin deviation is treated with the treatment composition. Treatment requires firing one or more of the nozzles of the nozzle array 100 which dispense the treatment composition onto the skin in the area of the skin deviation. Preferably the treatment composition is applied to the skin deviations in a discontinuous deposition pattern of discrete droplets between about 0.1μ to about 50μ in size. It is also preferred that no more than 95% of the skin deviation is covered by the treatment composition and more preferably no more than 85%. More specifically, the treatment composition is applied via the array of nozzles 100 and the local L is calculated along the length of, and in the firing range of, the array of nozzles 100. An individual nozzle may be fired to deposit the treatment composition, or multiple nozzles fired at the same time. The number of nozzles fired along the array of nozzles 100 can be adjusted based on the size of the ΔL and the size of the skin deviation. Furthermore the frequency of nozzle firing can be adjusted based on the ΔL, with more droplets being fired in succession in response to larger ΔL values. The array of nozzles can be a linear configuration, multiple rows, off-set, sine wave, curved, circular, or saw tooth arrangement.

Figure 11:
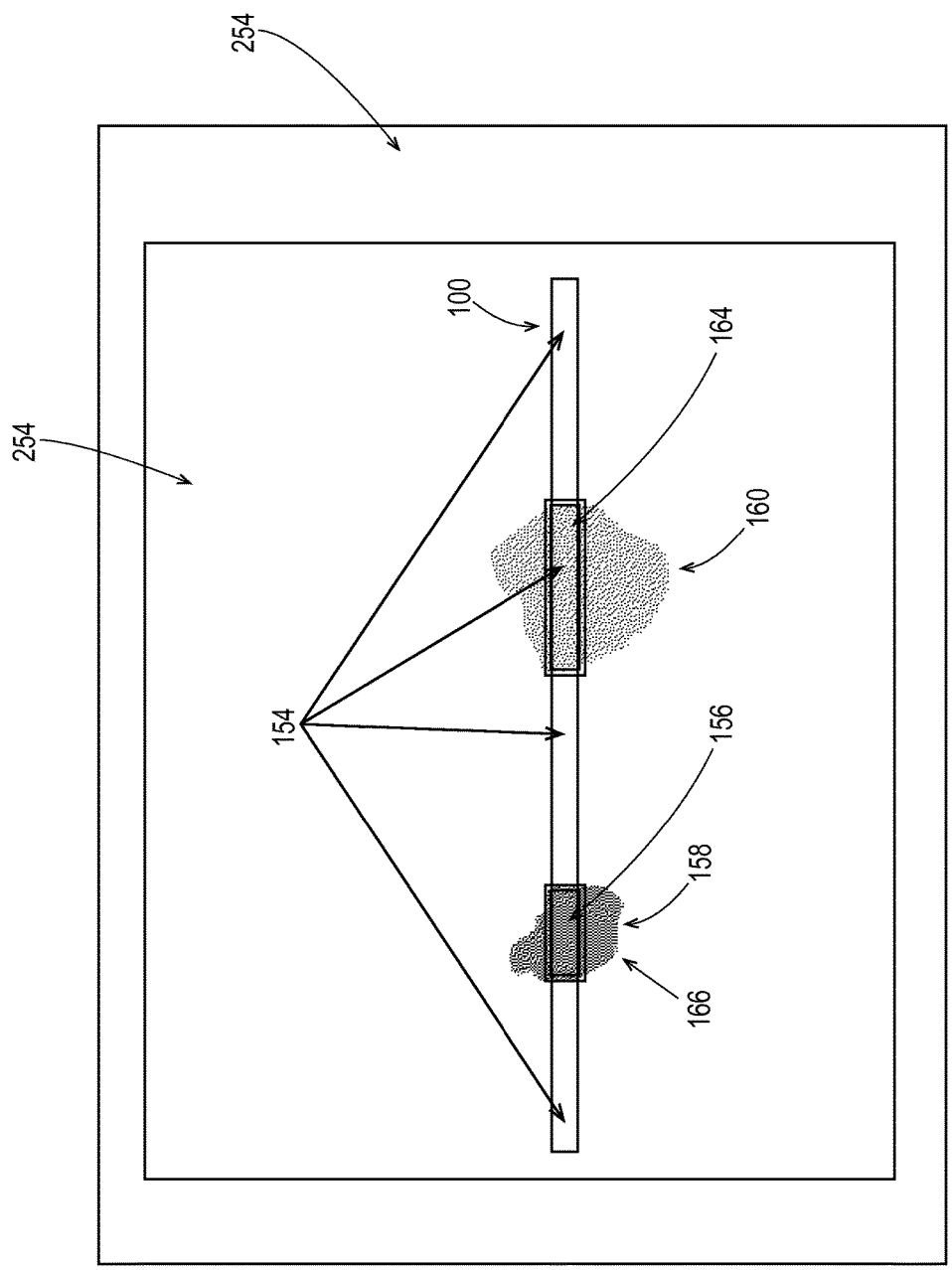
FIG. 11 illustrates a sample of skin being treated by the handheld treatment apparatus of FIG. 1 according to one or more embodiments described herein.

Referring now to FIG. 11, analytical window 150 is an area that comprises a sample of skin 152 and nozzle array 100. Nozzle array 100 contains individual nozzles that are off, i.e., not firing, 154, and individual nozzles that are firing 156. Skin deviations 158 and 160 are shown underneath the nozzle array 100. Background L is calculated on and around skin area 152, skin area 152 is where local $L_1$ is measured and skin area 166 is where local $L_2$ is measured. Skin area 164 is under nozzle array 100 but not within a skin deviation. Thus, the absolute value of local $L_1$–background L ($\Delta L_1$) is less than the preset threshold to initiate nozzle firing. The ΔL threshold required to initiate nozzle firing is a variable and is dependent on the scale used. For example, in a case where the 0-255 gray scale is utilized then the ΔL threshold required to initiate nozzle firing would commonly be a value of 2 or greater. Thus in the example shown in FIG. 11, the value of $\Delta L_1$ is less than 2. Likewise, skin area 166 is within skin deviation 158, and the absolute value of local $L_2$–background L ($\Delta L_2$) is greater than about 2. Thus the nozzles 154 around skin areas 152 and 164 are generally off, and the nozzles 156 around skin area 166 are generally firing. To insure the nozzles do not clog with particles or dried treatment composition, any nozzle can be fired at any time simply to keep it clean, i.e., not clogged and "healthy". And as discussed above, the number of nozzles directly over a skin deviation that are fired in response to the skin deviation can be adjusted based on the size of ΔL, the size (e.g., surface area) of the skin deviation or other parameters devised by those skilled in the art.

Figure 12:
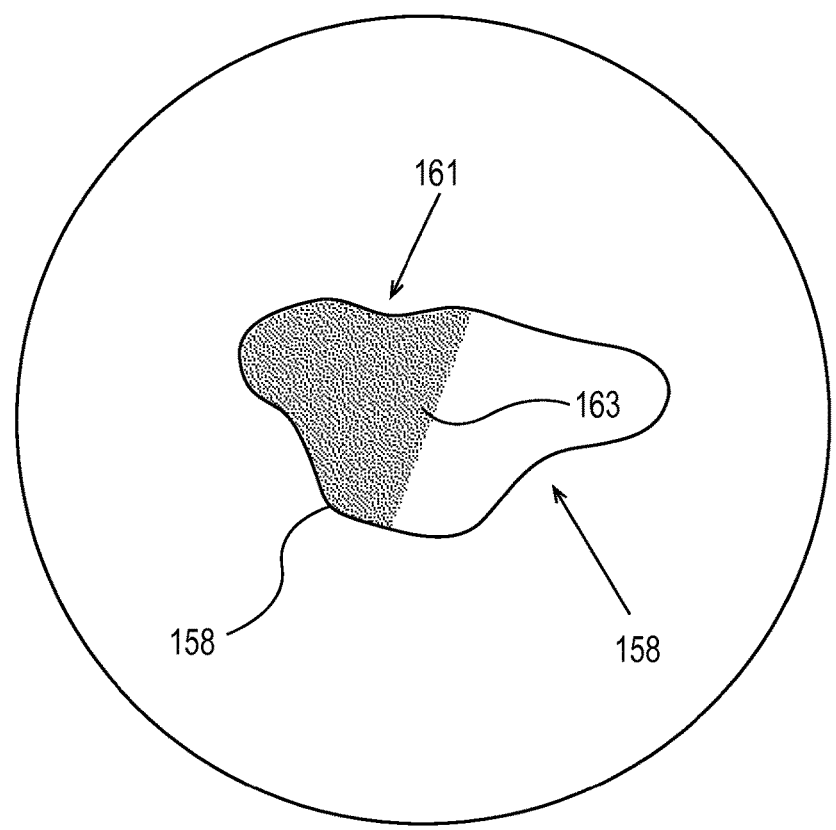
FIG. 12 illustrates an exemplary deposition pattern using the handheld treatment apparatus of FIG. 1.

Referring briefly to FIG. 12, it should be noted that the treatment composition is applied to the skin deviations in a discontinuous deposition pattern 161 of discrete droplets 163. FIG. 12 illustrates an exemplary deposition pattern 161 showing controlled randomness in the treatment composition delivery precision. This controlled randomness is due, at least in part, to the increased distance of the array of nozzles 100 (e.g., at least 8 mm) from the skin surface 152 and movement of the handheld treatment apparatus 10 over the skin deviation 158.

Figure 13:
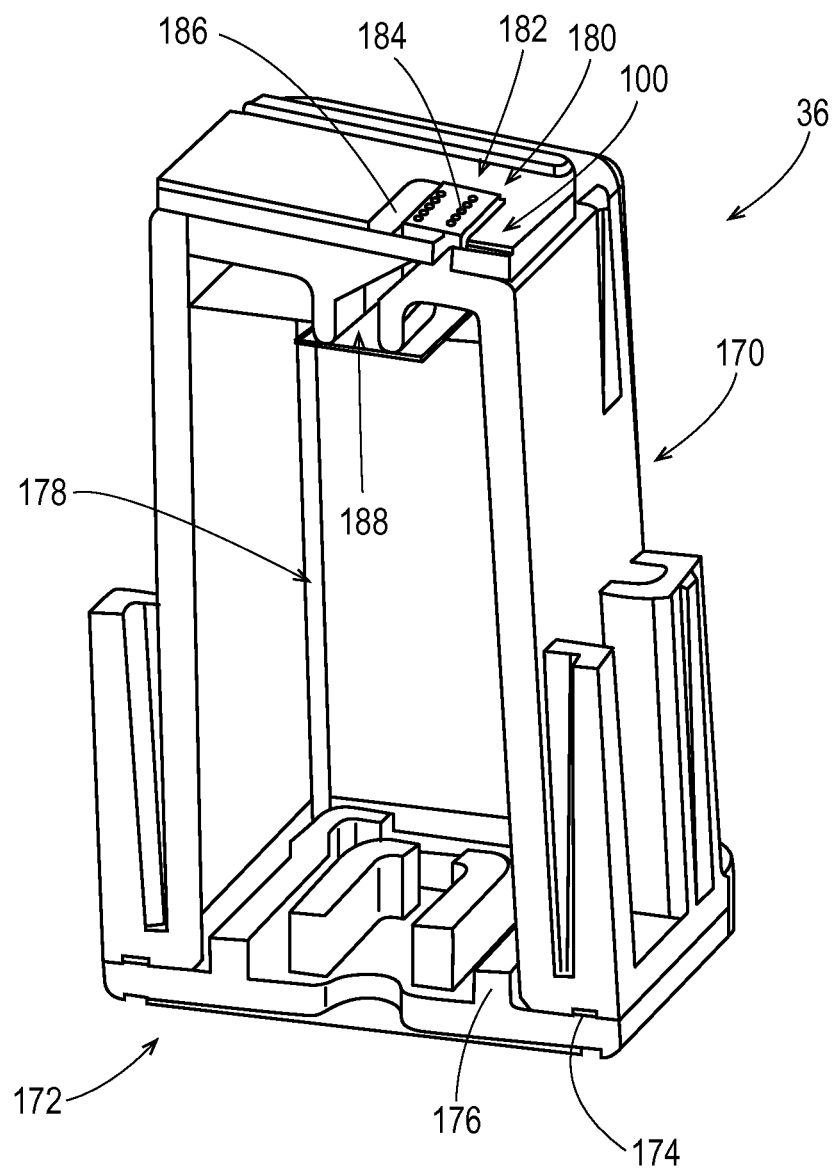
FIG. 13 is a section view of a cartridge for use with the handheld treatment device of FIG. 1 according to one or more embodiments described herein.

Referring now to FIG. 13, the exemplary cartridge 36 is illustrated including a cartridge body 170 and a cartridge cap 172 that is sealingly connected to the cartridge body 170 by a seal 174 and a plug 176 providing a friction fit between the cartridge cap 172 and cartridge body 170. The cartridge 36 may be considered unitary in that a composition reservoir 178 formed by the cartridge body 170 and print head 180 are formed within a single replaceable unit. In other embodiments, the cartridge 36 may not be replaceable. For example, the composition reservoir 178 may be refillable within the handheld treatment apparatus 10 or the composition reservoir 178 may be refillable when removed from the handheld treatment apparatus 10. The print head 180 may be a semiconductor device that includes a print head die 182 with the nozzle array 100 of a plurality of nozzles 184 fabricated on a semiconductor substrate 186, along with circuitry for addressing the nozzles 184 in response to signals from the processing unit 30. The treatment composition may be delivered from the composition reservoir 178, through a standpipe 188 and out any one or more of the nozzles 184, as described above. Print head die 182 may also be configured from substrates, printed circuit boards, silicon, glass, machineable glass ceramic, sapphire alumina, Liquid Crystal Polymer, polyimide and MEMS (MicroElectroMechanical Systems) devices. The composition reservoir 178 is in communication with the print head die 182 and the nozzles 100. Cartridge 36 may include more than one composition reservoir 178.

Figure 14:
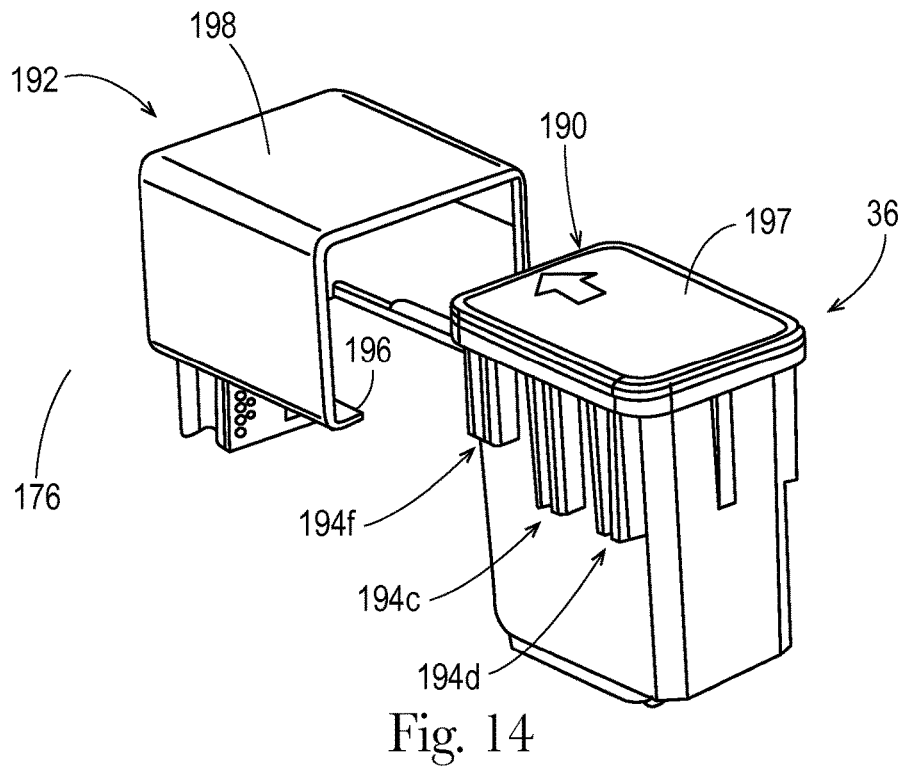
FIGS. 14-18 illustrate an exemplary method of inserting the cartridge of FIG. 13 into the handheld treatment device of FIG. 1 according to one or more embodiments described herein.

The cartridge 36 may include a visual cue 190 for indicating a proper direction for insertion of the cartridge 36 into a cartridge housing. FIGS. 14-18 depict interaction of the cartridge 36 with a cartridge housing 192, according to embodiments disclosed herein. As illustrated in FIG. 14, the cartridge 36 may be configured for insertion into the cartridge housing 192. Specifically, in order to ensure full insertion of the cartridge 36 into the cartridge housing 192, the cartridge 36 may include primary engagement rails 194a-194e, as well as an auxiliary engagement rail 194f. The cartridge housing 192 may include a securing rail 196 that is a predetermined length from a top 198 of the cartridge housing 192. The length between the securing rail 196 and the top 198 may substantially correspond with a length of the primary engagement rails 194a-194e (as measured from a top 197 of the cartridge 36) to allow for insertion of the cartridge 36 into the cartridge housing 192. Additionally, the cartridge housing 192 may include a blocking component 200 that extends from the securing rail 196 towards the top 198 of the cartridge housing 192. This blocking component 200 is arranged to allow the cartridge 36 to be fully inserted into the cartridge housing 192 when properly aligned because the auxiliary engagement rail 194f has a length that is shorter than the length of the primary engagement rails 194a-194e, allowing the cartridge 36 to pass the blocking component 200.

Figure 15:
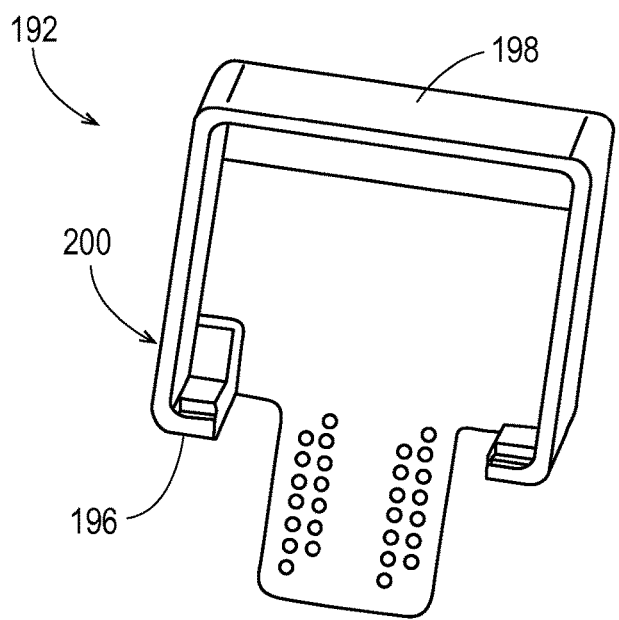

Depicted in FIG. 15 is a locking key mechanism 202, which engages the auxiliary engagement rail 194f to ensure that the cartridge 36 is properly inserted into the cartridge housing 192. Specifically, the locking key mechanism 202 may be configured to receive an electronic, software, or physical marker from the cartridge 36. If the marker is incorrect or missing, the cartridge housing 192 will indicate that the cartridge assembly 36 is not properly inserted.

Figure 16:
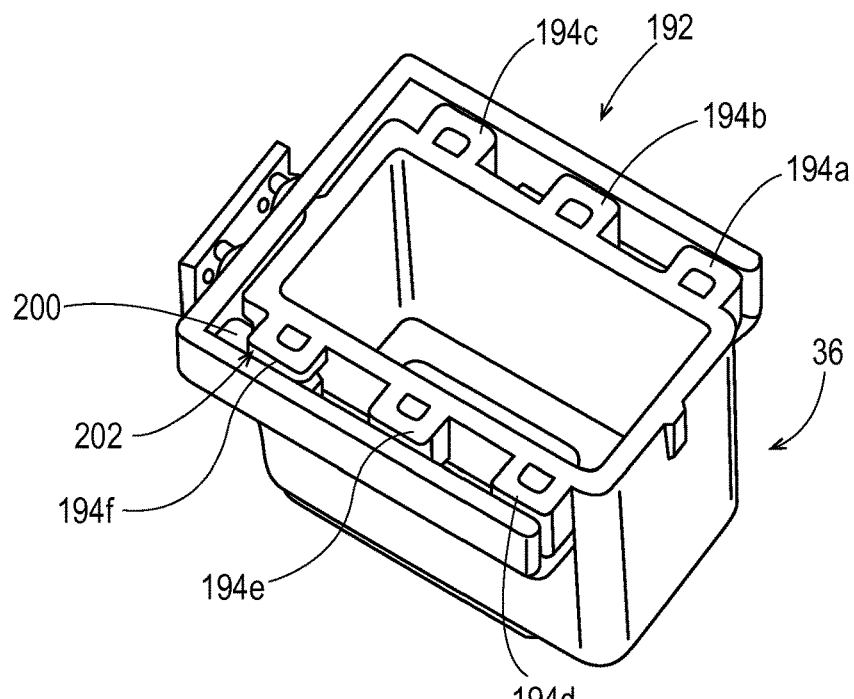

As illustrated in FIG. 16, the cartridge 36 has been properly inserted in to the cartridge housing 192. Accordingly, the auxiliary engagement rail 194f passes by the blocking component 200 to engage with the locking key mechanism 202.

Figure 17:
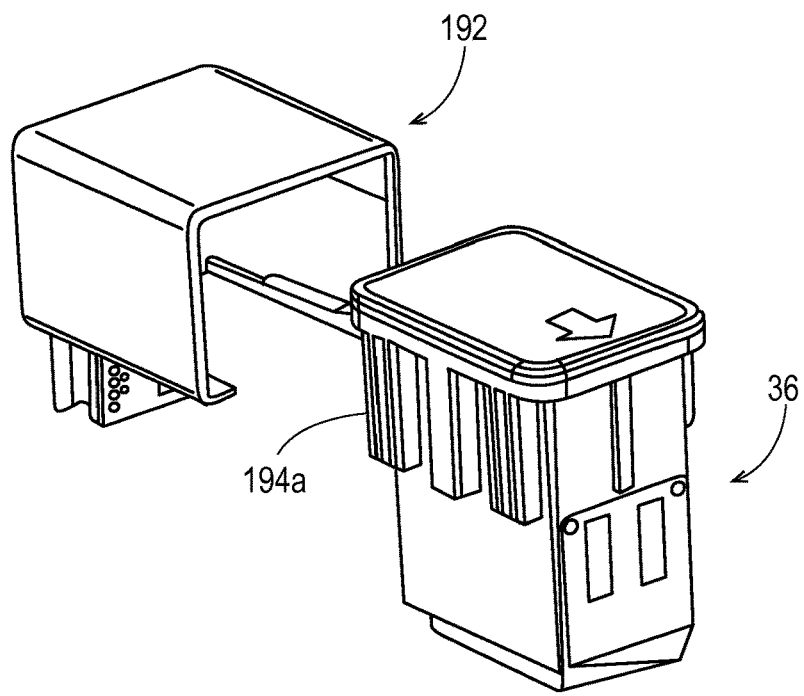
Figure 18:
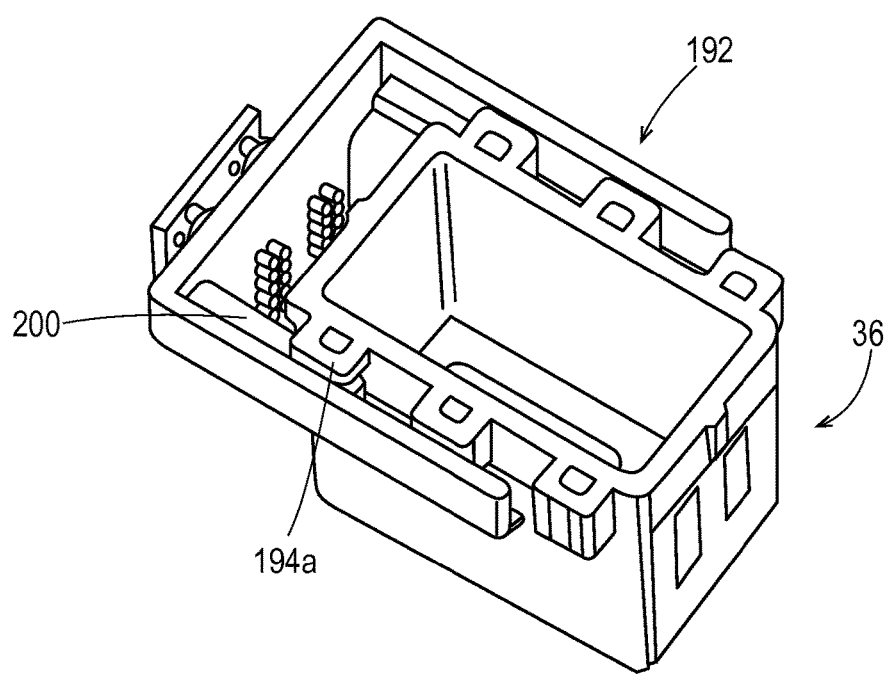

FIG. 17 illustrates that the cartridge 36 being improperly inserted into the cartridge housing 192. As a consequence, the primary engagement rail 194a will contact the blocking component 200, which prevents full insertion into the cartridge housing 192. Additionally, the locking key mechanism 202 will not receive the marker from the cartridge 36 to verify that the cartridge 36 is properly inserted. This is illustrated in FIG. 18, where the primary engagement rail 194a contacts the blocking component 200.

It should be understood that while some embodiments utilize the primary engagement rail 194a-194e and the auxiliary engagement rail 194f, this is merely an example. Some embodiments may utilize a primary engagement portion (one or more) and an auxiliary engagement portion (one or more) that extends from a surface of the cartridge 36 and provides similar function as the engagement rails 194. These engagement portions may not be shaped as depicted in the drawings herein, but instead may be shaped as notches that serve a similar function as the engagement rails 194. Accordingly, the auxiliary engagement portion may be positioned closer to a first end of the cartridge 36 (which may include an opposing first end and second end) than the primary engagement portion. This allows the cartridge 36 to pass the blocking component 200 for full insertion into the cartridge housing 192.

The treatment composition within cartridge body 170 may comprise particles and the treatment compositions preferably have a particle settling rate of less than 0.06 mm per day at 25° C. and 1 atm pressure. The treatment composition may further have an elastic modulus between about 0.1 Pa to about 1000 Pa at 25 C and 1000 Hz. Solid wax based treatment compositions may have an elastic modulus of up to about 100 MPa. In some embodiments, the particles in the treatment composition have a refractive index of between about 1.1 and about 5.0.

While inkjet cartridges are shown and exemplified herein, treatment compositions may be applied with other "flow control" devices or non-drop control devices. Flow control devices typically are characterized as "drop control techniques" where individual droplets of the substance are controlled. Ink jet printers, which are known to the art, are examples of drop on demand applicators and this technology is applicable for use the handheld treatment devices described herein. Spray devices and electrostatic spray devices are non-drop control techniques where droplets are produced and controlled only in aggregate. Often, in a spray device, a lack of individual droplet control, or "randomness" is desired in order to produce a smooth application over a relatively large area. By contrast, it is often desirable to provide very specific control of the amount and placement of the treatment compositions.

Examples of drop control include "fine flow control" where the flow of the substance is precisely controlled to deliver droplets as desired; and "inkjet technologies." An older inkjet technology includes supplying a continuous flow of charged droplets past electrostatic deflector plates which are alternately charged so that the plates either permit a droplet to pass or deflect to a gutter. This technique was the original design basis for inkjet printers. Other inkjet technologies include "drop on demand" such as thermal devices provided by Hewlett Packard, and piezoelectric devices such as provided by Epson and other printer manufacturers. In one embodiment, the drop on demand technology is combined with charging the droplets.

Equipment that might be useful in constructing the handheld treatment apparatus 10 are described in the following published patent applications: WO 2008/098234 A2, Handheld Apparatus and Method for the Automated Application of Cosmetics and Other Surfaces, first filed 11 Feb. 2007; WO 2008/100878 A1, System and Method for Applying a Treatment composition to Change a Person's Appearance Based on a Digital Image, first filed 12 Feb. 2007; WO 2008/098235 A2, System and Method for Providing Simulated Images Through Cosmetic Monitoring, first filed 11 Feb. 2007; WO 2008/100880 A1, System and Method for Applying Agent Electrostatically to Human Skin, first filed 12 Feb. 2007; US 2007/0049832 A1, System and Method for Medical Monitoring and Treatment Through Cosmetic Monitoring and Treatment, first filed 12 Aug. 2005; and US 2007/0035815 A1, System and Method for Applying a Treatment composition to Improve the Visual Attractiveness of Human Skin, first filed 12 Aug. 2005, all six applications filed by Edgar et al. The entire disclosure of each of the six Edgar et al. applications is incorporated herein by reference.

The treatment apparatuses described herein may be handheld but can be tethered to a structure that moves the apparatus across the keratinous surface to be modified. If handheld, the consumer would simply move the apparatus across the keratinous surface to be treated. Optionally, multiple apparatuses can be configured in a stationary structure wherein the consumer places the keratinous surface to be modified and multiple readings and applications occur simultaneously or in sequence.

The treatment composition can be applied to the keratinous surface by scanning and applying at the same time while making multiple passes over the surface. Several advantages result from using multiple pass application. The process for multiple pass applications is to make a partial application of the treatment composition, then to scan again the area of skin that has received the partial application. A further application of treatment compositions can be made, and still further multiple pass scanning and applications can be made to approach an aesthetic goal. Thus, the consumer can select the end point of the treatment, i.e. the "aesthetic goal", thus tailoring the treatment time to individual needs and preferences. Attempting to make all corrections in one treatment pass has been shown to overcorrect in certain areas.

It may be desirable for the apparatus to treat from about 1.0% to about 10% of the keratinous surface that is read by the sensor with a treatment composition. And the applicator may apply the first treatment composition in droplets having an average diameter of from about from about 0.1 μm to about 50 μm.

A variety of treatment compositions may be used, for example, inks, dyes, pigments, adhesives, curable compositions, optically activated compounds (for example, semiconductor quantum dots), metal oxides (for example, $TiO_2$), hollow spheres, bleaching agents, texture reducing polymers, skin care compositions, hair colorants, hair removal compositions (often referred to as depilatories), hair growth stimulants and mixtures thereof.

The treatment compositions can be delivered alone or in the presence of a dermatologically-acceptable carrier. The phrase "dermatologically-acceptable carrier", as used herein, means that the carrier is suitable for topical application to the keratinous tissue, has good aesthetic properties, is compatible with any additional components of the skin care composition, and will not cause any untoward safety or toxicity concerns. The carrier can be in a wide variety of forms. Non-limiting examples include simple solutions (water or oil based), emulsions, and solid forms (gels, sticks, flowable solids, wax, amorphous materials). In certain embodiments, the dermatologically acceptable carrier is in the form of an emulsion. Emulsion may be generally classified as having a continuous aqueous phase (e.g., oil-in-water and water-in-oil-in-water) or a continuous oil phase (e.g., water-in-oil and oil-in-water-in-oil). The oil phase may comprise silicone oils, non-silicone oils such as hydrocarbon oils, esters, ethers, and the like, and mixtures thereof. For example, emulsion carriers can include, but are not limited to, continuous water phase emulsions such as silicone-in-water, oil-in-water, and water-in-oil-in-water emulsion; and continuous oil phase emulsions such as water-in-oil and water-in-silicone emulsions, and oil-in-water-in-silicone emulsions. The treatment composition can be delivered in a variety of product forms including, but not limited to, a cream, a lotion, a gel, a foam, a paste, or a serum. Additionally, the treatment composition can include for purposes of proper formulation and stabilization anti-fungal, anti-microbial, and anti-bacterial components.

The treatment compositions may include humectants as a carrier or chassis for the other components in the treatment composition. An exemplary class of humectants is polyhydric alcohols. Suitable polyhydric alcohols include polyalkylene glycols and alkylene polyols and their derivatives, including propylene glycol, dipropylene glycol, polypropylene glycol, polyethylene glycol and derivatives thereof; sorbitol; hydroxypropyl sorbitol; erythritol; threitol; pentaerythritol; xylitol; glucitol; mannitol; butylene glycol (e.g., 1,3-butylene glycol); pentylene glycol; hexane triol (e.g., 1,2,6-hexanetriol); glycerin; ethoxylated glycerine; and propoxylated glycerine.

Other suitable humectants include sodium 2-pyrrolidone-5-carboxylate, guanidine; glycolic acid and glycolate salts (e.g., ammonium and quaternary alkyl ammonium); lactic acid and lactate salts (e.g., ammonium and quaternary alkyl ammonium); aloe vera in any of its variety of forms (e.g., aloe vera gel); hyaluronic acid and derivatives thereof (e.g., salt derivatives such as sodium hyaluronate); lactamide monoethanolamine; acetamide monoethanolamine; urea; sodium pyroglutamate, water-soluble glyceryl poly(meth) acrylate lubricants (such as Hispagel®) and mixtures thereof.

Inks, dyes, metal oxides and pigments (collectively referred to as "colorants" below) are used to modify the color or reflectance of the keratinous surface. These compositions are commonly used to modify color and reflectance in cosmetic, "make-up" compositions. Foundation, lipstick, eyeliner are just a few examples of these compositions, but they are all applied evenly across large portions of the keratinous surface, that is they are macro-applications. In sharp contrast, the present treatment compositions are selectively applied on a very small scale to select areas, that is, a micro application. Suitable colorants may include inorganic or organic pigments and powders. Organic pigments can include natural colorants and synthetic monomeric and polymeric colorants. Organic pigments include various aromatic types such as azo, indigoid, triphenylmethane, anthraquinone, and xanthine dyes which are designated as D&C and FD&C blues, browns, greens, oranges, reds, yellows, etc. Organic pigments may consist of insoluble metallic salts of certified color additives, referred to as the Lakes. Inorganic pigments include iron oxides, ferric ammonium ferrocyanide, manganese violet, ultramarines, chromium, chromium hydroxide colors, and mixtures thereof. The pigments may be coated with one or more ingredients that cause the pigments to be hydrophobic. Suitable coating materials that will render the pigments more lipophilic in nature include silicones, lecithin, amino acids, phospholipids, inorganic and organic oils, polyethylene, and other polymeric materials. Suitable silicone treated pigments as disclosed in U.S. Pat. No. 5,143,722. Inorganic white or uncolored pigments include $TiO_2$, $ZnO$, $ZrO_2$, hollow spheres or semiconductor quantum dots, which are commercially available from a number of sources. Other suitable colorants are identified in U.S. Pat. No. 7,166,279. Colorants are generally included at a weight percent such that the skin care composition yields a perceptible color. The colorant particle shape is typically spherical, polygonal or fractal. In one embodiment, the skin care composition exhibits a color that perceptibly different from the color of the applicator. By perceptibly different, refers to a difference in color that is perceptible to a person having normal sensory abilities under standard lighting conditions (e.g., natural illumination as experienced outdoors during daylight hours, the illumination of a standard 100 watt incandescent or equivalent LED white light bulb at a distance of 2 meters, or as defined by CIE D65 standard illuminate lighting at 800 lux to a 1964 CIE standard observer).

Adhesives that are compatible with keratinous surfaces are known and any such adhesive can be applied with the handheld treatment apparatus 10. Commercially available adhesives compatible with keratinous surfaces are available from the 3M Corporation of Minneapolis Minn. See, for example: U.S. Pat. No. 6,461,467, issued to Blatchford, et al., filed on Apr. 23, 2001; U.S. Pat. No. 5,614,310, issued to Delgado, et al., filed on Nov. 4, 1994; and U.S. Pat. No. 5,160,315, issued to Heinecke et al., filed on Apr. 5, 1991. The entire disclosures of these patent applications are incorporated by reference. After the adhesive is selectively applied to the keratinous surface, a second treatment composition can be dusted on the keratinous surface where it will stick to the adhesive. The second modification that is not adhered to the keratinous surface can then be removed leaving behind a selective, micro application of the second treatment composition. Likewise compositions that cure upon exposure to certain wavelengths of energy, infrared light or ultraviolet (uv) for example, can be applied. By this method, the curable composition is selectively applied to the keratinous surface and then it is cured by exposing the keratinous surface to the curing energy source. The entire keratinous surface can be exposed, or the exposure can be done at the same time as the application.

Wrinkle or texture reducing polymers and skin tightening may be used. See, for example: U.S. Pat. No. 6,139,829, issued to Estrin on Oct. 31, 2000; and US Patent Applications US20060210513A1, filed by Luizzi, et al. on Mar. 21, 2005; US20070224158A1, filed by Cassin et al. on Mar. 18, 2005; and US20070148120A1, filed by Omura et al. on Jan. 14, 2005. The entire disclosures of this patent and these published patent applications are incorporated by reference. More specifically, a cosmetic process for softening the wrinkles of wrinkled skin may comprise applying, to the wrinkled skin, a cosmetic composition, in particular an anti-wrinkle composition, comprising, in a physiologically acceptable medium suitable for topical application to the skin of the face: from 0.1 to 20% by weight of at least one tensioning agent, with respect to the total weight of the composition.

Optically-activated particles can be used as or added to the treatment compositions. Sometimes referred to a "interference pigments", these particles include a plurality of substrate particles selected from the group consisting of nylons, acrylics, polyesters, other plastic polymers, natural materials, regenerated cellulose, metals, hollow spheres, semiconductor quantum dots and minerals; an optical brightener chemically bonded to each of the plurality of substrate particles to form integral units in the form of optically-activated particles for diffusing light. These particles help to reduce the visual perception of skin imperfections, including cellulite, shadows, skin discolorations, and wrinkles. Each of the optically-activated particles are encapsulated with a UV transparent coating to increase the diffusion of light to further reduce the visual perception of the skin imperfections. The encapsulated optically-activated particles are able to absorb ultraviolet radiation and emit visible light; and the encapsulated optically-activated particles are able to both scatter and absorb light in a diffuse manner in order to reduce the visual perception of skin imperfections, including cellulite, wrinkles, shadows, and skin discolorations, when the optically-activated particles are applied to the skin surface.

Hair colorants and hair removal compositions are also suitable for use with the handheld treatment apparatus. These compositions, and their component parts, may be described by the examples given below. Each of the individual chemical compositions described below for hair colorants can be used in combination with any of the others ingredients, and likewise, those skilled in the art will appreciate that the individual compositions given for depilatories can be used with other ingredients listed in other examples.

Skin care compositions can be applied with the handheld treatment apparatus 10. The skin care composition may be used as, for example, a moisturizer, a conditioner, an anti-aging treatment, a skin lightening treatment, a sunscreen, a sunless tanner, and combinations thereof. The skin care composition may comprise a safe and effective amount of one or more skin care active ("active") useful for regulating and/or improving skin condition. "Safe and effective amount" means an amount of a compound or composition sufficient to induce a positive benefit but low enough to avoid serious side effects (i.e., provides a reasonable benefit to risk ratio within the judgment of a skilled artisan). A safe and effective amount of a skin care active can be from about $1 \times 10^{-6}$ to about 25% by weight of the total composition, in another embodiment from about 0.0001 to about 25% by weight of the total composition, in another embodiment from about 0.01 to about 10% by weight of the total composition, in another embodiment from about 0.1 to about 5% by weight of the total composition, in another embodiment from about 0.2 to about 2% by weight of the total composition. Suitable actives include, but are not limited to, vitamins (e.g., B3 compounds such as niacinamide, niacin-nicotinic acid, tocopheryl nicotinate; B5 compounds, such as panthenol; vitamin A compounds and natural and/or synthetic analogs of Vitamin A, including retinoids, retinol, retinyl acetate, retinyl palmitate, retinoic acid, retinaldehyde, retinyl propionate, carotenoids (pro-vitamin A); vitamin E compounds, or tocopherol, including tocopherol sorbate, tocopherol acetate; vitamin C compounds, including ascorbate, ascorbyl esters of fatty acids, and ascorbic acid derivatives such as magnesium ascorbyl phosphate and sodium ascorbyl phosphate, ascorbyl glucoside, and ascorbyl sorbate), peptides (e.g., peptides containing ten or fewer amino acids, their derivatives, isomers, and complexes with other species such as metal ions), sugar amines (e.g., N-acetyl-glucosamine), sunscreens, oil control agents, tanning actives, anti-acne actives, desquamation actives, anti-cellulite actives, chelating agents, skin lightening agents, flavonoids, protease inhibitors (e.g., hexamidine and derivatives), non-vitamin antioxidants and radical scavengers, peptides, salicylic acid, hair growth regulators, anti-wrinkle actives, anti-atrophy actives, minerals, phytosterols and/or plant hormones, tyrosinase inhibitors, N-acyl amino acid compounds, moisturizers, plant extracts, and derivatives of any of the aforementioned actives. The term "derivative" as used herein refers to structures which are not shown but which one skilled in the art would understand are variations of the basic compound. For example, removing a hydrogen atom from benzene and replacing it with a methyl group. Suitable actives are further described in U.S. application publication No. US2006/0275237A1 and US2004/0175347A1.

Herein, "contrast ratio" refers to the opacity of the composition, or the ability of the composition to reduce or prevent light transmission, determined after the composition is drawn onto an opacity chart (Form N2A, Leneta Company of Manwah, N.J. or the equivalent thereof), and by using a spectrophotometer with settings selected to exclude specular reflection. The composition is applied to the top of the opacity chart and then is drawn into a film having a thickness of approximately 0.01 inches using a film applicator (e.g., as commercially available from BYK Gardner of Columbia, Md., or the equivalent thereof). The film is allowed to dry for 2 hours under conditions of 22° C.+/−1° C., 1 atm. Using a spectrophotometer, the Y tristimulus value (i.e., the XYZ color space of the film) of the product film is measured and recorded. The Y tristimulus value is measured in three different areas of the product film over the black section of the opacity chart, and also in three different areas of the product film over the white section of the opacity chart.

The contrast ratio for the individual layers, that is the contrast ratio for the first layer or the powder layer is less than about 20, preferably less than about 10, and even more preferably less than about 6.

The contrast ratio is calculated as the mathematical average of the three Y tristimulus values over the black areas, divided by the mathematical average of the three Y tristimulus values over the white areas, times 100:

$$\text{Contrast Ratio} = \frac{\text{average }(Y black)}{\text{average }(Y white)} \times 100$$

EXAMPLES

The following examples further describe and demonstrate various embodiments. The examples are given solely for the purpose of illustration and are not to be construed as limitations, as many variations thereof are possible.

The following 9 Examples are all treatment compositions. They can be applied by any of the methods and apparatuses described herein, such as via a thermal ink jet printer head and cartridge combination.

Example 1

Treatment Composition

| Phase | ingredient | description | wt % |
|---|---|---|---|
| A | Water | water | 64.80 |
| A | Veegum HS | Magnesium Aluminum Silicate | 2.00 |
| B | Propylene Glycol | Propylene Glycol | 15.00 |
| B | PEG-2M | PEG2M | 0.10 |
| C | GLW45GYAP (yellow iron oxide) | 45% Iron Oxide slurry in glycerin/water | 0.60 |
| C | GLW75PFAP-MP | 75% TiO2 slurry in glycerin/water | 15.00 |
| C | PVP/VA W 735 | 50% VP/VA Copolymer in water | 1.50 |
| D | Symdiol | Hexanediol/Caprylyl glycol | 1.00 |

Combine ingredients of phase A using a homogenizer for mixing and sifting the Veegum into the water. Begin heating water to 75 C. Continue to mix for 20 min at 75 C. Then, shut off heat. Combine phase B in a separate container and add to phase A with mixing while phase A cools. Add components of phase C one at a time to phase A/B while it continues to cool. When temperature reaches approximately 50 C, add phase D while continuing to mix. Mix for 2-3 minutes to ensure homogeneity then pour into container.

Example 2

Treatment Composition

| Phase | ingredient | description | wt % |
|---|---|---|---|
| A | Water | water | 66.40 |
| A | Veegum HS | Magnesium Aluminum Silicate | 0.50 |
| B | Propylene Glycol | Propylene Glycol | 15.00 |
| B | GLW45GYAP (yellow iron oxide) | 45% Iron Oxide slurry in glycerin/water | 0.60 |
| B | GLW75PFAP-MP | 75% TiO2 slurry in glycerin/water | 15.00 |
| B | PVP/VA W 735 | 50% VP/VA Copolymer in water | 1.50 |
| C | Symdiol | Hexanediol/Caprylyl glycol | 1.00 |

Combine ingredients of phase A using a homogenizer for mixing and sifting the Veegum into the water. Begin heating water to 75 C. Continue to mix for 20 min at 75 C. Then, shut off heat. Add components of phase B one at a time to phase A while it continues to cool. When temperature reaches approximately 50 C, add phase C while continuing to mix. Mix for 2-3 minutes to ensure homogeneity then pour into container.

Example 3

Treatment Composition

| phase | ingredient | description | wt % |
|---|---|---|---|
| A | Water | water | 68.25 |
| A | Veegum Ultra | Magnesium Aluminum Silicate | 0.50 |
| B | Propylene Glycol | Propylene Glycol | 13.50 |
| B | Sicovit Yellow Iron Oxide | 100% Yellow Iron Oxide | 0.25 |
| B | GLW75PFAP-MP | 75% TiO2 slurry in glycerin/water | 15.00 |
| B | PVP/VA W 735 | 50% VP/VA Copolymer in water | 1.50 |
| C | Symdiol | Hexanediol/Caprylyl glycol | 1.00 |

Combine ingredients of phase A using a homogenizer for mixing and sifting the Veegum into the water. Begin heating water to 75 C. Continue to mix for 20 min at 75 C. Then, shut off heat. Add components of phase B one at a time to phase A while it continues to cool. When temperature reaches approximately 50 C, add phase C while continuing to mix. Mix for 2-3 minutes to ensure homogeneity then pour into container.

Example 4

Treatment Composition

| phase | ingredient | description | wt % |
|---|---|---|---|
| A | Propylene Glycol | Propylene Glycol | 15.00 |
| A | Versaflex V-150 | Steareth-100, Steareth-2, Mannan, Xanthan Gum | 0.50 |
| B | Water | Water | 66.75 |
| B | Symdiol | Hexanediol/Caprylyl glycol | 1.00 |
| C | Sicovit Yellow Iron Oxide | 100% Yellow Iron Oxide | 0.25 |
| C | GLW75PFAP-MP | 75% TiO2 slurry in glycerin/water | 15.00 |
| C | PVP/VA W 735 | 50% VP/VA Copolymer in water | 1.50 |

Combine ingredients of phase A until uniform. Slowly add components of phase B one at a time with mixing. Add components of phase C one at a time using homogenizer to phase A/B to ensure uniformity and even dispersion. Mix for 2-3 minutes then pour into container.

Example 5

Treatment Composition

| phase | ingredient | description | wt % |
|---|---|---|---|
| A | Water | water | 70.23 |
| A | Veegum Ultra | Magnesium Aluminum Silicate | 0.40 |
| B | Propylene Glycol | Propylene Glycol | 12.50 |
| B | Sodium Carboxymethyl Cellulose 7L2P | Cellulose Gum | 0.40 |
| C | Sicovit Yellow Iron Oxide | 100% Yellow Iron Oxide | 0.22 |
| C | Sachtleben RC402 | Titanium Dioxide | 13.75 |
| C | PVP/VA W 735 | 50% VP/VA Copolymer in water | 1.50 |
| D | Symdiol | Hexanediol/Caprylyl glycol | 1.00 |

Combine ingredients of phase A using a homogenizer for mixing and sifting the Veegum into the water. Begin heating water to 75 C. Continue to mix for 20 min at 75 C. Then, shut off heat. Combine phase B in a separate container and add to phase A with mixing while phase A cools. Add components of phase C one at a time to phase A/B while it continues to cool. When temperature reaches approximately 50 C, add phase D while continuing to mix. Mix for 2-3 minutes to ensure homogeneity then pour into container.

Example 6

Treatment Composition

| phase | ingredient | description | wt % |
|---|---|---|---|
| A | Water | water | 65.80 |
| A | Veegum HS | Magnesium Aluminum Silicate | 2.00 |
| B | Propylene Glycol | Propylene Glycol | 15.00 |
| B | Natrosol 250 LR | Hydroxyethylcellulose | 0.50 |
| B | PEG-2M | PEG2M | 0.10 |
| C | GLW45GYAP (yellow iron oxide) | 45% Iron Oxide slurry in glycerin/water | 0.60 |
| C | GLW75PFAP-MP | 75% TiO2 slurry in glycerin/water | 15.00 |
| D | Symdiol | Hexanediol/Caprylyl glycol | 1.00 |

Combine ingredients of phase A using a homogenizer for mixing and sifting the Veegum into the water. Begin heating water to 75 C. Continue to mix for 20 min at 75 C. Then shut off heat. Combine phase B in a separate container and add to phase A with mixing while phase A cools. Add components of phase C one at a time to phase A/B while it continues to cool. When temperature reaches approximately 50 C, add phase D while continuing to mix. Mix for 2-3 minutes to ensure homogeneity then pour into container.

Example 7

Treatment Composition

| phase | ingredient | description | wt % |
|---|---|---|---|
| A | Water | water | 70.08 |
| A | Veegum Ultra | Magnesium Aluminum Silicate | 0.40 |
| B | Propylene Glycol | Propylene Glycol | 12.50 |
| B | Keltrol CG-T | Xanthan Gum | 0.05 |
| C | Sicovit Yellow Iron Oxide | 100% Yellow Iron Oxide | 0.22 |
| C | Sachtleben RC402 | Titanium Dioxide | 13.75 |
| C | PVP K15 | 30% PVP in water | 2.00 |
| D | Symdiol | Hexanediol/Caprylyl glycol | 1.00 |

Combine ingredients of phase A using a homogenizer for mixing and sifting the Veegum into the water. Begin heating water to 75 C. Continue to mix for 20 min at 75 C. Then, shut off heat. Combine phase B in a separate container and add to phase A with mixing while phase A cools. Add components of phase C one at a time to phase A/B while it continues to cool. When temperature reaches approximately 50 C, add phase D while continuing to mix. Mix for 2-3 minutes to ensure homogeneity then pour into container.

Example 8

Treatment Composition

| phase | ingredient | description | wt % |
|---|---|---|---|
| A | Propylene Glycol | Propylene Glycol | 15.00 |
| A | Versaflex V-150 | Steareth-100, Steareth-2, Mannan, Xanthan Gum | 0.50 |
| B | Water | Water | 64.90 |
| B | Symdiol | Hexanediol/Caprylyl glycol | 1.00 |
| C | Sicovit Yellow Iron Oxide | 100% Yellow Iron Oxide | 2.00 |
| C | Sicovit Red Iron Oxide | 100% Red Iron Oxide | 0.10 |
| C | GLW75PFAP-MP | 75% TiO2 slurry in glycerin/water | 15.00 |
| C | PVP/VA W 735 | 50% PVP/VA Copolymer in water | 1.50 |

Combine ingredients of phase A until uniform. Slowly add components of phase B one at a time with mixing. Add components of phase C one at a time using homogenizer to phase A/B to ensure uniformity and even dispersion. Mix for 2-3 minutes then pour into container.

Example 9

Treatment Composition

| phase | ingredient | description | wt % |
|---|---|---|---|
| A | Water | water | 61.25 |
| A | Veegum HS | Magnesium Aluminum Silicate | 2.00 |
| B | Propylene Glycol | Propylene Glycol | 15.00 |
| B | PEG-2M | Polyethylene Glycol | 0.10 |
| C | GLW45GYAP (yellow iron oxide) | 45% Iron Oxide slurry in glycerin/water | 4.00 |
| C | GLW55GRAP (red iron oxide) | 55% Iron Oxide slurry in glycerin/water | 0.15 |
| C | GLW75PFAP-MP | 75% TiO2 slurry in glycerin/water | 15.00 |
| C | PVP/VA W 735 | 50% PVP/VA Copolymer in water | 1.50 |
| D | Symdiol | 50/50 Hexanediol/Caprylyl glycol | 1.00 |

Combine ingredients of phase A using a homogenizer for mixing and sifting the Veegum into the water. Begin heating water to 75 C. Continue to mix for 20 min at 75 C. Then, shut off heat. Combine phase B in a separate container and add to phase A with mixing while phase A cools. Add components of phase C one at a time to phase A/B while it continues to cool. When temperature reaches approximately 50 C, add phase D while continuing to mix. Mix for 2-3 minutes to ensure homogeneity then pour into container.

As indicated above, maintenance of the handheld treatment apparatus 10 can be important, for example, to prevent clogging of the nozzle array 100 and, in some embodiments, to charge the battery 24 for continued use. In some embodiments, battery recharging may be accomplished by direct current via a wired connection, or by wireless charging via induction techniques. For example, it may be undesirable to store the handheld treatment device in an upstanding orientation on the base 16 (FIG. 1). To this end, the base 16 may be angled or some other surface contour to prevent a user from standing the handheld treatment apparatus 10 upright on its base 16.

Referring to FIG. 19, a docking station 250 may be provided. The docking station 250 may include a station base 252, a charging assembly 254 and a docking unit 256 that can be assembled to the station base 252. The docking unit 256 may include one or more compartments 258 and 260 that are configured to receive the handheld treatment apparatus 10 in a desired orientation, while preventing docking of the handheld treatment apparatus 10 in other orientations, such as upright, as noted above, or on its side. The charging assembly 254 may provide electrical contacts 262 to facilitate an electrical connection between the handheld treatment apparatus 10 and an electrical supply outlet. The charging assembly may also provide for wirelessly charging handheld treatment apparatus 10

Referring to FIG. 20, the docking station 250 may further include its own processing unit 270, one or more sensors 272 and a communications unit 274. The sensors 272 may provide a number of indications to the processing unit 270, such as presence or absence of the handheld treatment apparatus 10 and proper or improper insertion of the handheld treatment apparatus 10 in the docking station, charge of the battery 24, fill level of the cartridge 36, etc. A user interface 278, such as a display, lights, speakers, etc. may be provided to provide signals based on the inputs of the sensors 272. For example, if the processing unit 270 determines absence of the handheld treatment apparatus 10 for a preselected time, an indication may be provided by the docking station 250 and/or the handheld treatment apparatus 10 itself, for example, using the communications unit 274 that is paired with the handheld treatment apparatus 10. In some embodiments, the communications unit 274 may be capable of communications with the user through other means, such as via a wireless network. Wireless communications may be performed via Wireless Local Area Networks (WLAN) and Wireless Personal Area Networks (WPAN) WLAN networks use the IEEE 802.11 standards, typically known as WI-FI, which is intended for replacement of high speed cabling via wireless communications. WPAN networks use the Bluetooth Special Interest Group standards, which are intended for wireless communication between portable equipment or fixed equipment (for example a home thermostat) and its applications, and Near Field Communication (NFC) communication technology under standards from for example, the NFC Forum. Dreamworks products may also use wireless RFD (Radio Frequency Identification) communication technology with standards from a number of regulatory bodies, including International Organization for Standards (ISO), International Electrotechnical Commission (IEC), ASTM international, DASH7 Alliance and EPC Global, for example. WPAN is also known as LAN (Local Area Networks) or WLAN (Wireless Local Area Networks), which is a wireless computer network that links two or more devices using a wireless distribution method within a limited area such as a home, school, or office space, etc. A piconet is a computer network which links a wireless user group of devices using Bluetooth technology protocols. For example, a piconet could include a Dreamworks device connected to a smart phone or a cell phone connected to a computer, a laptop and a Bluetooth-enabled sensor (for example, a digital camera). For example, the docking station 250 may generate an SMS, email or even call the user upon occurrence of a predetermined event. In some embodiments, a vibration unit 280 may be provided that can be used to vibrate the handheld treatment apparatus 10, for example, at predetermined intervals.

Referring to FIG. 21, to further facilitate maintenance of the handheld treatment apparatus 10, a cap assembly 300 may be provided. The cap assembly 300 may include any number of components, such as cap body 302, primary cap component 304 that connects to the cap body 302 and a secondary cap component 306 that connects to the primary cap component 304. A nozzle seal member 308 may be provided including a sealing portion 310 and a reservoir portion 312. The sealing portion 310 can seal against the applicator head 20 and the nozzle array 100. The reservoir portion 312 can allow for periodic discharge of the nozzle array 100, while containing the treatment composition and inhibiting leakage.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any embodiments disclosed, or in any combination with any other reference or references, teaches, suggests or discloses any such embodiments. Further, to the extent that any meaning or definition of a term in this document conflicts with any meaning or definition of the same term in a document incorporated by reference, the meaning or definition assigned to that term in this document shall govern.

While particular embodiments have been illustrated and described, it would be obvious to those skilled in the art that various other changes and modifications can be made without departing from the spirit and scope of the claims. It is therefore intended to cover in the appended claims all such changes and modifications that are within the scope of this specification.

What is claimed is:

1. An applicator head releasably connectable to an outer housing of an apparatus for treating human skin, the applicator head comprising:
   a body having a housing connector end configured to releasably connect to the outer housing and a skin engaging end having an opening therethrough for delivering a skin treatment composition through the opening in the applicator head onto human skin; and
   a pair of skin engagement members arranged and configured to flatten a surface of the skin, wherein the pair of skin engagement members comprises a first roller at a first side of the opening and a second roller at a second, opposite side of the opening, wherein each of the first and second rollers is connected to the applicator head at a pivot axis, wherein the distance between the pivot axes of the first and second rollers is between about 5 mm and about 15 mm.

2. The applicator head of claim 1, wherein a gap between the first and second rollers is no greater than about 10 mm.

3. The applicator head of claim 1, wherein the first and second rollers share a tangent plane that defines an imaginary flat rolling surface.

4. The applicator head of claim 1, wherein the opening is no greater than about 100 mm².

5. The apparatus of claim 1 including a battery.

* * * * *